(12) United States Patent
Brachman et al.

(10) Patent No.: US 12,053,644 B2
(45) Date of Patent: Aug. 6, 2024

(54) RADIATION SHIELDING APPARATUS FOR IMPLANTABLE RADIOACTIVE SEEDS

(71) Applicant: GT MEDICAL TECHNOLOGIES, INC., Tempe, AZ (US)

(72) Inventors: David Brachman, Phoenix, AZ (US); John Baker, Gilbert, AZ (US); Heidi Cole, Phoenix, AZ (US); Adam Turner, Phoenix, AZ (US)

(73) Assignee: GT Medical Technologies, Inc., Tempe, AZ (US)

(*) Notice: Subject to any disclaimer, the term of this patent is extended or adjusted under 35 U.S.C. 154(b) by 0 days.

(21) Appl. No.: 17/936,149

(22) Filed: Sep. 28, 2022

(65) Prior Publication Data
US 2023/0211176 A1 Jul. 6, 2023

Related U.S. Application Data

(60) Provisional application No. 63/295,316, filed on Dec. 30, 2021.

(51) Int. Cl.
*A61N 5/10* (2006.01)
*G21F 3/00* (2006.01)

(52) U.S. Cl.
CPC .......... *A61N 5/1007* (2013.01); *A61N 5/1015* (2013.01); *G21F 3/00* (2013.01); *A61N 2005/1024* (2013.01); *A61N 2005/1094* (2013.01)

(58) Field of Classification Search
CPC ................ A61N 5/1007; A61N 5/1015; A61N 2005/1024; A61N 2005/1094; G21F 3/00
USPC ........................................................ 600/1–8
See application file for complete search history.

(56) References Cited

U.S. PATENT DOCUMENTS

| | | | |
|---|---|---|---|
| D244,393 S | 5/1977 | Collica et al. |
| 4,509,506 A | 4/1985 | Windorski et al. |
| 4,706,652 A | 11/1987 | Horowitz |
| 4,754,745 A | 7/1988 | Horowitz |
| 4,946,435 A | 8/1990 | Suthanthiran et al. |
| 5,030,195 A | 7/1991 | Nardi |
| D381,080 S | 7/1997 | Ohata |
| 5,772,574 A | 6/1998 | Nanko |
| 5,803,895 A | 9/1998 | Kronholz et al. |
| 5,840,008 A | 11/1998 | Klein et al. |

(Continued)

FOREIGN PATENT DOCUMENTS

| | | |
|---|---|---|
| BR | 11 2013 027841 2 | 4/2012 |
| CA | 2835065 | 2/2018 |

(Continued)

OTHER PUBLICATIONS

Cole, P.D., et al., "A comparative long-term assessment of four soft tissue supplements". Anesthetic Surg J. 31(6). 674-681, 2011.

(Continued)

*Primary Examiner* — Sunita Reddy
(74) *Attorney, Agent, or Firm* — Knobbe, Martens, Olson & Bear, LLP

(57) ABSTRACT

The disclosure is directed to devices for use in radiation therapy. Various configurations of shielding materials within shielding layers, such as for use in shielding radiation from radioactive sources within implanted radioactive carriers, are discussed herein.

19 Claims, 22 Drawing Sheets

(56) References Cited

U.S. PATENT DOCUMENTS

| | | |
|---|---|---|
| 5,871,708 A | 2/1999 | Park et al. |
| D408,957 S | 4/1999 | Sandor |
| 5,967,966 A | 10/1999 | Kronholz et al. |
| 5,997,842 A | 12/1999 | Chen |
| 6,017,482 A | 1/2000 | Anders et al. |
| D420,452 S | 2/2000 | Cardy |
| D420,745 S | 2/2000 | Cardy |
| D420,746 S | 2/2000 | Cardy |
| 6,066,302 A | 5/2000 | Bray |
| 6,129,670 A | 10/2000 | Burdette et al. |
| D443,061 S | 5/2001 | Bergstrom et al. |
| 6,248,057 B1 | 6/2001 | Mavity et al. |
| 6,273,851 B1 | 8/2001 | Slater et al. |
| 6,293,899 B1 | 9/2001 | Sioshansi et al. |
| 6,327,490 B1 | 12/2001 | Spetz |
| 6,352,500 B1 | 3/2002 | Halpern |
| 6,358,195 B1 | 3/2002 | Green et al. |
| 6,360,116 B1 | 3/2002 | Jackson et al. |
| 6,385,477 B1 | 5/2002 | Werner et al. |
| 6,450,937 B1 | 9/2002 | Mercereau et al. |
| 6,471,631 B1 | 10/2002 | Slater et al. |
| 6,512,943 B1 | 1/2003 | Kelcz |
| 6,539,247 B2 | 3/2003 | Spetz |
| 6,547,816 B1 | 4/2003 | O'Foghludha |
| 6,572,526 B1 | 6/2003 | Ford |
| 6,666,811 B1 * | 12/2003 | Good ................. C23C 14/30 427/5 |
| 6,679,824 B1 * | 1/2004 | Reed ................. A61P 35/00 600/7 |
| 6,712,508 B2 | 3/2004 | Nilsson et al. |
| 6,712,782 B2 | 3/2004 | Ford |
| D488,864 S | 4/2004 | Fago et al. |
| 6,761,680 B2 | 7/2004 | Terwillieger et al. |
| 6,770,021 B2 | 8/2004 | Halpern |
| 6,787,042 B2 | 9/2004 | Bond et al. |
| 6,790,170 B2 | 9/2004 | Moody et al. |
| 6,846,282 B1 | 1/2005 | Ford |
| 6,994,688 B2 | 2/2006 | Brauckman et al. |
| 7,011,619 B1 | 3/2006 | Lewis |
| 7,070,554 B2 | 7/2006 | White et al. |
| 7,118,729 B1 | 10/2006 | O'Foghludha |
| 7,190,895 B1 | 3/2007 | Groves et al. |
| D561,896 S | 2/2008 | Jones |
| 7,410,458 B2 | 8/2008 | Bray et al. |
| 7,442,162 B2 | 10/2008 | Henderson et al. |
| D580,056 S | 11/2008 | Orthner |
| D580,057 S | 11/2008 | Ramadani |
| 7,686,756 B2 | 3/2010 | Black et al. |
| 7,736,293 B2 | 6/2010 | Lamoureux et al. |
| 7,749,151 B2 | 7/2010 | Ferguson |
| 7,776,310 B2 | 8/2010 | Kaplan |
| 7,972,261 B2 | 7/2011 | Lamoureux et al. |
| 8,012,455 B2 | 9/2011 | O'Foghludha |
| 8,021,291 B2 | 9/2011 | Lamoureux et al. |
| 8,039,790 B2 | 10/2011 | Cho et al. |
| 8,097,236 B2 | 1/2012 | Aston et al. |
| 8,114,007 B2 | 2/2012 | Lamoureux et al. |
| D657,474 S | 4/2012 | Dona |
| 8,187,159 B2 | 5/2012 | Lamoureux et al. |
| 8,192,345 B2 | 6/2012 | Lamoureux et al. |
| 8,226,539 B2 | 7/2012 | Cutrer |
| 8,293,630 B2 | 10/2012 | Dunkley et al. |
| 8,323,172 B2 | 12/2012 | Black et al. |
| 8,366,598 B2 | 2/2013 | Lamoureux et al. |
| D680,649 S | 4/2013 | Jagger et al. |
| D681,210 S | 4/2013 | Beiriger et al. |
| D681,812 S | 5/2013 | Farris et al. |
| D681,813 S | 5/2013 | Jagger et al. |
| 8,454,489 B2 | 6/2013 | Drobnik et al. |
| D686,341 S | 7/2013 | Nakaji et al. |
| D686,744 S | 7/2013 | Nakaji et al. |
| D686,745 S | 7/2013 | Nakaji et al. |
| D686,746 S | 7/2013 | Nakaji et al. |
| D686,747 S | 7/2013 | Nakaji et al. |
| D686,748 S | 7/2013 | Nakaji et al. |
| D687,568 S | 8/2013 | Nakaji et al. |
| D687,966 S | 8/2013 | Nakaji et al. |
| D687,967 S | 8/2013 | Nakaji et al. |
| 8,600,130 B2 | 12/2013 | Järliden |
| 8,605,966 B2 | 12/2013 | Järliden |
| 8,647,603 B2 | 2/2014 | Aston et al. |
| 8,771,162 B2 | 7/2014 | Lamoureux et al. |
| 8,790,235 B2 | 7/2014 | Lamoureux et al. |
| 8,795,146 B2 | 8/2014 | Lamoureux et al. |
| 8,825,136 B2 | 9/2014 | Giller et al. |
| 8,827,884 B2 | 9/2014 | Ribbing et al. |
| 8,834,837 B2 | 9/2014 | Kelson et al. |
| 8,876,684 B1 | 11/2014 | Nakaji et al. |
| 8,878,464 B2 | 11/2014 | Clayton et al. |
| 8,894,969 B2 | 11/2014 | Kelson et al. |
| 8,915,834 B1 | 12/2014 | Lamoureux et al. |
| 8,939,881 B2 | 1/2015 | Nakaji et al. |
| 8,974,364 B1 | 3/2015 | Nakaji et al. |
| 9,022,914 B2 | 5/2015 | Clayton et al. |
| 9,022,915 B2 | 5/2015 | Nakaji et al. |
| 9,180,310 B2 | 11/2015 | Black et al. |
| 9,358,377 B2 | 6/2016 | Black et al. |
| 9,403,033 B1 | 8/2016 | Brachman |
| 9,409,038 B2 | 8/2016 | Nakaji et al. |
| 9,492,683 B2 | 11/2016 | Brachman et al. |
| 9,526,463 B2 | 12/2016 | Brachman et al. |
| 9,545,525 B2 | 1/2017 | Nakaji et al. |
| 9,642,999 B2 | 5/2017 | Sutton et al. |
| 9,788,909 B2 | 10/2017 | Larkin et al. |
| 9,789,608 B2 | 10/2017 | Itkowitz et al. |
| 9,808,650 B2 | 11/2017 | White et al. |
| 9,821,174 B1 | 11/2017 | Fram et al. |
| 10,058,713 B2 | 8/2018 | Kelson et al. |
| 10,080,909 B2 | 9/2018 | Brachman et al. |
| 10,085,699 B2 | 10/2018 | Brachman et al. |
| 10,265,542 B2 | 4/2019 | Brachman et al. |
| 10,328,278 B2 | 6/2019 | Krachon et al. |
| 10,335,613 B2 | 7/2019 | Dikaiou |
| 10,350,431 B2 | 7/2019 | Nakaji et al. |
| 10,449,386 B2 | 10/2019 | Bask et al. |
| 10,646,724 B2 | 5/2020 | Hoedl et al. |
| 10,888,710 B1 | 1/2021 | Brachman et al. |
| 10,974,069 B2 | 4/2021 | Maguire et al. |
| 10,981,018 B2 | 4/2021 | Baker et al. |
| 11,224,761 B1 * | 1/2022 | Wazer ................. A61N 5/1007 |
| 11,278,736 B2 | 3/2022 | Brachman et al. |
| 11,298,846 B1 | 4/2022 | Hanberg et al. |
| 2001/0044567 A1 | 11/2001 | Zamora et al. |
| 2002/0055666 A1 | 5/2002 | Hunter |
| 2002/0058854 A1 | 5/2002 | Reed et al. |
| 2002/0120174 A1 | 8/2002 | Steele, Sr. et al. |
| 2003/0045769 A1 | 3/2003 | Kalas et al. |
| 2003/0088141 A1 | 5/2003 | Terwilliger et al. |
| 2003/0109769 A1 * | 6/2003 | Lowery ............. A61M 37/0069 600/7 |
| 2003/0113359 A1 | 6/2003 | Iyer et al. |
| 2003/0130573 A1 | 7/2003 | Yu et al. |
| 2003/0149329 A1 | 8/2003 | O'Foghludha |
| 2003/0208096 A1 | 11/2003 | Tam |
| 2004/0091421 A1 | 5/2004 | Aston et al. |
| 2004/0109823 A1 * | 6/2004 | Kaplan ................. A61L 31/02 600/1 |
| 2004/0116767 A1 | 6/2004 | Lebovic et al. |
| 2004/0225176 A1 | 11/2004 | Flanagan et al. |
| 2004/0242953 A1 | 12/2004 | Good |
| 2005/0035310 A1 | 2/2005 | Drobnik et al. |
| 2005/0111621 A1 | 5/2005 | Riker et al. |
| 2005/0244045 A1 | 11/2005 | Eriksson |
| 2005/0267319 A1 | 12/2005 | White et al. |
| 2006/0015030 A1 | 1/2006 | Poulin et al. |
| 2006/0058570 A1 * | 3/2006 | Rapach ................. A61P 31/00 600/7 |
| 2006/0063962 A1 | 3/2006 | Drobnik et al. |
| 2006/0173236 A1 | 8/2006 | White et al. |
| 2006/0224035 A1 | 10/2006 | Russell, Jr. et al. |
| 2006/0235365 A1 | 10/2006 | Terwilliger |
| 2006/0253048 A1 | 11/2006 | Jones |
| 2007/0135673 A1 | 6/2007 | Elliott et al. |

(56) References Cited

U.S. PATENT DOCUMENTS

| | | |
|---|---|---|
| 2007/0167665 A1* | 7/2007 | Hermann ............ A61N 5/1027 600/3 |
| 2007/0190761 A1 | 8/2007 | Dunkley et al. |
| 2007/0225544 A1 | 9/2007 | Vance et al. |
| 2008/0004714 A1 | 1/2008 | Lieberman |
| 2008/0009661 A1 | 1/2008 | Lamoureux et al. |
| 2008/0058580 A1 | 3/2008 | Black et al. |
| 2008/0146861 A1 | 6/2008 | Murphy et al. |
| 2008/0221384 A1 | 9/2008 | Chi Sing et al. |
| 2009/0012347 A1 | 1/2009 | Helle |
| 2009/0069625 A1 | 3/2009 | Helle et al. |
| 2009/0131735 A1 | 5/2009 | Drobnik et al. |
| 2009/0136422 A1 | 5/2009 | Kelson et al. |
| 2009/0156880 A1 | 6/2009 | Allan et al. |
| 2009/0234177 A1 | 9/2009 | Lebovic et al. |
| 2009/0253950 A1 | 10/2009 | Rapach et al. |
| 2009/0271715 A1 | 10/2009 | Tumuluri |
| 2009/0275793 A1 | 11/2009 | Black et al. |
| 2010/0015042 A1 | 1/2010 | Keisari et al. |
| 2010/0056843 A1 | 3/2010 | Fisher et al. |
| 2010/0056908 A1 | 3/2010 | Giller et al. |
| 2010/0200778 A1 | 8/2010 | Drobnik et al. |
| 2010/0228074 A1 | 9/2010 | Drobnik et al. |
| 2010/0268015 A1 | 10/2010 | Drobnik et al. |
| 2010/0288916 A1 | 11/2010 | Cho et al. |
| 2010/0324353 A1 | 12/2010 | Helle |
| 2011/0013818 A1 | 1/2011 | Eriksson Järliden |
| 2011/0206252 A1 | 8/2011 | Eriksson Järliden |
| 2012/0108882 A1* | 5/2012 | Hoedl ................ A61N 5/1001 600/3 |
| 2012/0165957 A1 | 6/2012 | Everland et al. |
| 2013/0102832 A1 | 4/2013 | Hoedl et al. |
| 2013/0102891 A1 | 4/2013 | Binnekamp et al. |
| 2013/0131434 A1 | 5/2013 | Nakaji et al. |
| 2013/0209965 A1 | 8/2013 | Fisker |
| 2013/0338423 A1 | 12/2013 | Nakaji et al. |
| 2014/0275716 A1 | 9/2014 | Brachman et al. |
| 2014/0296612 A1 | 10/2014 | Schwartz |
| 2014/0316187 A1 | 10/2014 | Nakaji et al. |
| 2015/0057487 A1 | 2/2015 | Nakaji et al. |
| 2015/0105605 A1 | 4/2015 | Finger et al. |
| 2015/0140535 A1 | 5/2015 | Geri et al. |
| 2015/0157879 A1 | 6/2015 | Wu et al. |
| 2015/0196778 A1 | 7/2015 | Nakaji et al. |
| 2015/0321024 A1 | 11/2015 | Nakaji et al. |
| 2015/0367144 A1 | 12/2015 | Flynn et al. |
| 2016/0242855 A1 | 8/2016 | Fichtinger et al. |
| 2016/0367709 A1 | 12/2016 | Aston et al. |
| 2017/0021191 A1 | 1/2017 | Brachman et al. |
| 2017/0113064 A1 | 4/2017 | Hingston et al. |
| 2017/0120073 A1 | 5/2017 | Brachman et al. |
| 2017/0215824 A1* | 8/2017 | Brachman ................ G21F 1/12 |
| 2017/0252575 A1 | 9/2017 | Nakaji et al. |
| 2018/0063386 A1 | 3/2018 | Sharma et al. |
| 2018/0333509 A1 | 11/2018 | Aston et al. |
| 2018/0345038 A1 | 12/2018 | Kelson et al. |
| 2019/0018148 A1 | 1/2019 | Ueno et al. |
| 2019/0143143 A1* | 5/2019 | Abdalla ............... A61N 5/1007 600/3 |
| 2019/0240504 A1 | 8/2019 | Brachman et al. |
| 2020/0047001 A1 | 2/2020 | Nakaji et al. |
| 2020/0086141 A1 | 3/2020 | Finger et al. |
| 2020/0206372 A1 | 7/2020 | Aston et al. |
| 2020/0261740 A1 | 8/2020 | Baker et al. |
| 2020/0261741 A1* | 8/2020 | Herskovic ............ A61N 5/1007 |
| 2020/0406059 A1 | 12/2020 | Kelson et al. |
| 2021/0008233 A1 | 1/2021 | Kelson et al. |
| 2021/0128945 A1 | 5/2021 | Schmidt et al. |
| 2021/0154340 A1 | 5/2021 | Kelson et al. |
| 2021/0183492 A1 | 6/2021 | Park |
| 2021/0236850 A1 | 8/2021 | Baker et al. |
| 2021/0353960 A1 | 11/2021 | Sienko et al. |
| 2021/0370083 A1 | 12/2021 | Giladi et al. |
| 2021/0379096 A1 | 12/2021 | Domankevich et al. |
| 2022/0096854 A1 | 3/2022 | Carlson |
| 2022/0184418 A1 | 6/2022 | Arazi et al. |
| 2022/0212035 A1 | 7/2022 | Kelson et al. |

FOREIGN PATENT DOCUMENTS

| | | |
|---|---|---|
| CA | 2834559 | 11/2018 |
| CA | 3017174 | 1/2020 |
| DE | 613 528 | 5/1935 |
| EP | 0 292 630 B1 | 8/1995 |
| EP | 0 906 769 A2 | 4/1999 |
| EP | 1 330 292 | 7/2003 |
| EP | 2 968 884 | 1/2016 |
| EP | 2701803 B1 | 8/2018 |
| EP | 3456384 | 3/2019 |
| JP | S52-9424 | 7/1975 |
| JP | H09-028810 | 4/1997 |
| JP | 2001-266903 | 9/2001 |
| JP | 3095304 | 7/2003 |
| JP | 2007-512112 | 5/2007 |
| JP | 2009-515603 | 4/2009 |
| JP | 2010-536529 | 12/2010 |
| JP | 6365983 | 7/2018 |
| WO | WO 01/87418 | 11/2001 |
| WO | WO 2007/106531 A1 | 9/2007 |
| WO | WO 2012/100206 A2 | 7/2012 |
| WO | WO 2012/149580 A1 | 11/2012 |
| WO | WO 2012/154988 | 11/2012 |
| WO | WO 2016/171961 | 10/2016 |
| WO | WO 2016/179420 | 11/2016 |

OTHER PUBLICATIONS

International Search Report; International Application No. PCT/US2012/035907, mailed on Sep. 26, 2012; 3 pages.

International Search Report; International Application No. PCT/US2012/035909, mailed on Aug. 30, 2012; 3 pages.

Crepeau, R.H., et al., "Image Processing of Imperfect Protein Arrays: Sectioned Crystals and Tubulin Sheets and Rings". Elec. Microsc. Soc. Amer. Proc. 40:84-87, 1982.

Crepeau, R.H., et al., "Reconstruction of imperfectly ordered zinc-induced tubulin sheets using cross-correlation and real space averaging". Ultramicroscopy, 6, 7-18, 1981.

Dagnew, E., et al., "Management of newly diagnosed single brain metastasis using resection and permanent iodine-125 seeds without initial whole-brain radiotherapy: a two institution experience". Neurosurg Focus. 15; 22(3):E3, 2007.

Delaney, T.F., et al., "Intraoperative dural irradiation by customized 192 iridium and 90 Yttrium brachytherapy plaques". Int. J. Radiat Oncol Biol Phys. 57(1): 239-245, 2003.

Ewersten, et al., "Biopsy Guided by Real-Time Sonography Fused with MRI: A Phantom Study", American Journal of Roentgenology. 2008; 190: 1672-1674. 10.2214/AJR.07.2587.

Gutin, P.H., et al., "A coaxial catheter system for after loading radioactive sources for the interstitial irradiation of brain tumors. Technical note". J. Neurosurg 56: 734-735, 1982.

Gutin, P.H., et al., "Brachytherapy of recurrent tumors of the skull base and spine with iodine-125 sources". Neurosurgery 20:938-945, 1987.

Hamilton, A.J., et al., "The use of gold foil wrapping for radiation protection of the spinal cord for recurrent tumor therapy". Int. J. Radiat Oncol Biol Phys. 32(2):507-511, 1995.

Hilaris, B.S., et al., "Interstitial irradiation for unresectable carcinoma of the lung". Ann Thoracic Surg; 20:491-500, 1975.

Hilaris, B.S., et al., "Intraoperative radiotherapy in stage I and II lung cancer". Semin Surg Oncol. 3:22-32, 1987.

Huang, K., et al., "Surgical resection and permanent iodine-125 brachytherapy for brain metastases". J. Neurooncol. 91:83-93, 2009.

Jenkins, H.P., et al., "Clinical and experimental observations on the use of a gelatin sponge or foam". Surg 20:124-132, 1946.

Kneschaurek, P. et al.: "Die Flabmethode Zur Intraoperativen Bestrahlung. Öthe Flab-Method for Intraoperative Radiation Therapy", Strahlentherapie und Oknologie, Urban Und Vogel, Muenchen, DE, vol. 171, No. 2; Feb. 1, 1995, pp. 61-69, XP000610565, ISSN:0179-7158.

(56) References Cited

OTHER PUBLICATIONS

Marchese, M.J., et al., "A versatile permanent planar implant technique utilizing iodine-125 seeds imbedded in gelfoam". Int J Radiat Oncol Biol Phys 10:747-751, 1984.

Miller, S., et al., "Advances in the virtual reality interstitial brachytherapy system." Engineering Solutions for the Next Millenium. 1999 IEEE Canadian Conference on Electrical and Computer Engineering (Cat. No. 99TH8411). vol. 1. IEEE, 1999.

Murphy, M.K., et al., "Evaluation of the new cesium-131 seed for use in low-energy x-ray brachytherapy". Med Phy 31(6): 1529-1538, Jun. 2004.

Nori, D., et al., "Intraoperative brachytherapy using Gelfoam radioactive plaque implants for resected stage III non-small-cell lung cancer with positive margin: A pilot study". J Surg Oncol. 60:257-261, 1995.

Parashar, B., et al., "Cesium-131 permanent seed brachytherapy: Dosimetric evaluation and radiation exposure to surgeons, radiation oncologists, and staff". Brachytherapy. 10:508-511, 2011.

Patel, S., et al., "Permanent iodine-125 interstitial implants for the treatment of recurrent Glioblastoma Multiforme". Neurosurgery 46 (5) 1123-1128, 2000.

Rivard, M.J., "Brachytherapy dosimetry parameters calculated for a 131 Cs source". Med Phys. 34(2): 754-765, 2007.

Rogers, C.L., et al., "Surgery and permanent 125-1 seed paraspinal brachytherapy for malignant tumors with spinal cord compression". Int. J. Radial Oncol Biol Phys. 54(2): 505-513, 2002.

Wernicke, A.G., et al., "Feasibility and safety of Gliasite brachytherapy in the treatment of CNS tumors following neurosurgical resection". J. Cancer Res Ther. 6(1), 65-74, Jan.-Mar. 2010.

CivaSheet; "Precision Therapy Without The Beam"; CivaTech Oncology Inc.; CivaTech; https://civatechoncology.com/professionals/civasheet/2 pages; Accessed on Oct. 2018.

CivaSheet; "Precision Therapy Without The Beam"; CivaTech Oncology Inc.; CivaTech; https://civatechoncology.com/products-2/products/; 5 pages; Accessed on Oct. 2018.

Aima, Manik et al.; "Dosimetric Characterization of a New Directional Low-Dose Rate Brachytherapy Source"; Department of Medical Physics; Mar. 11, 2018; 32 pages.

Rivard, Mark J.; "A Directional Pd Brachytherapy Device: Dosimetric Characterization and Practical Aspects for Clinical Use"; Department of Radiation Oncology; Brachytherapy 16 (2017) pp. 421-432.

Office Action dated Apr. 2, 2015; European Patent Application No. 12724426.7; 5 pages.

Office Action dated Oct. 30, 2015; European Patent Application No. 12724426.7; 4 pages.

Office Action dated Feb. 9, 2016; Japanese Application No. 2014-508190; 7 pages including english translation.

International Search Report; International Application No. PCT/US2016/031035; filed May 5, 2016; 15 pages; mailed on Aug. 5, 2016.

International Search Report and Written Opinion; International Application No. PCT/US2016/027143, filed Apr. 12, 2016; mailed on Aug. 25, 2016; 7 pages.

Decision of Rejection dated Feb. 4, 2016, Japanese Patent Application No. 2014-508190 with English Translation; 4 pages.

Search and Examination Report; Application No. P1140/13; Filed on Oct. 24, 2013 (PCT Apr. 30, 2012); 10 pages.

Summons to Attend Oral Proceedings dated Aug. 18, 2017; European Application No. 12724426.7; 5 pages.

Office Action dated Nov. 2, 2017; European Patent Application No. 12724427.5; 4 pages.

Extended European Search Report; Application No. 18186392.9; dated Jan. 7, 2019; 7 pages.

\* cited by examiner

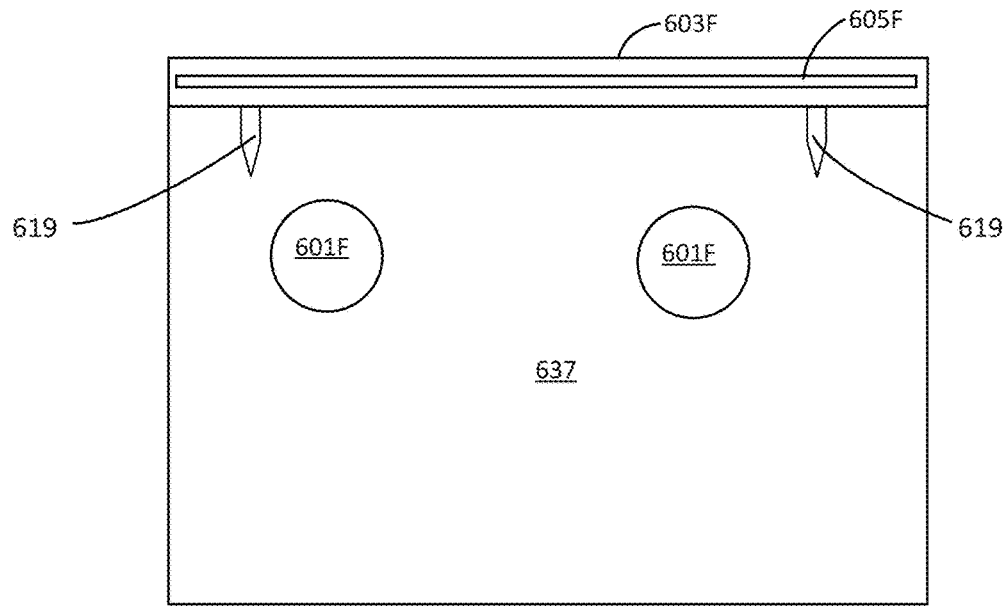
FIGURE 6E
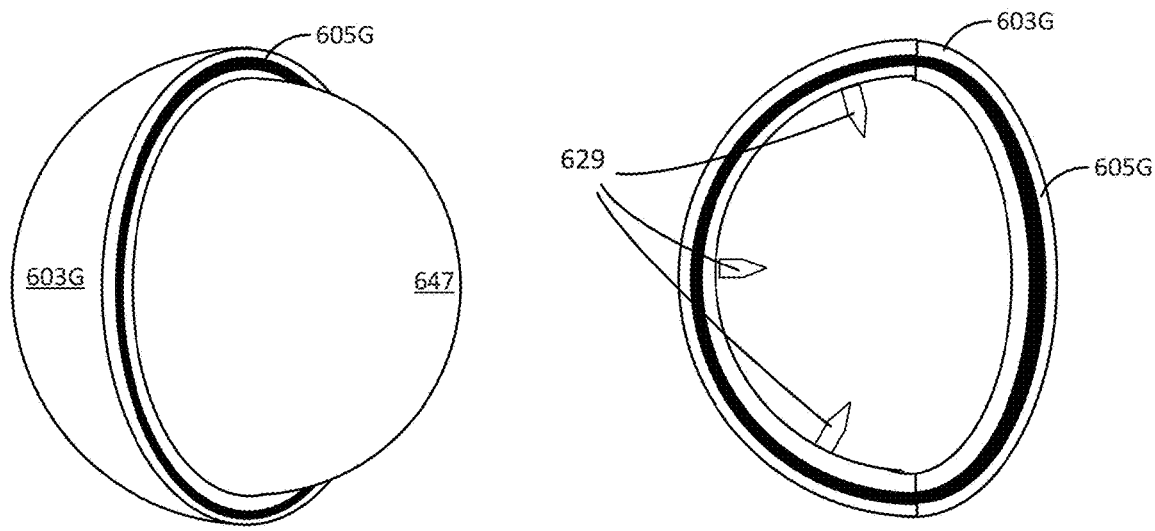
FIGURE 6F
FIGURE 6G

End View

Side View

Top View

RADIATION SHIELDING APPARATUS FOR IMPLANTABLE RADIOACTIVE SEEDS

PRIORITY CLAIM

This application is a non-provisional of and claims priority to U.S. Provisional Patent Application No. 63/295,316, filed Dec. 30, 2021, entitled "RADIATION SHIELDING APPARATUS FOR IMPLANTABLE RADIOACTIVE SEEDS." The disclosure of the foregoing application is hereby incorporated by reference in its entirety.

FIELD OF THE DISCLOSURE

The present disclosure generally relates to devices used in conjunction with radiation therapy.

BACKGROUND

Tumors in living organisms are highly variable in size, location and their amount of infiltration into normal tissues, the variability of tumors in general make them very difficult to treat with a one-size fits all approach. Furthermore, the extent of tumors and/or void upon debulking are typically not known until presented in the operating room. Thus, the options necessary to effectively treat a tumor or tumor bed need to be quite diverse.

Brachytherapy involves placing a radiation source either into or immediately adjacent to a tumor. It provides an effective treatment of cancers of many body sites. Brachytherapy, as a component of multimodality cancer care, provides cost-effective treatment. Brachytherapy may be intracavitary, such as when treating gynecologic malignancies; intraluminal, such as when treating esophageal or lung cancers; external surface, such as when treating cancers of the skin, or interstitial, such as when treating various central nervous system tumors as well as extracranial tumors of the head and neck, lung, soft tissue, gynecologic sites, rectum, liver, prostate, penis and skin.

SUMMARY

Various embodiments of systems, methods and devices within the scope of the appended claims each have several aspects, no single one of which is solely responsible for the desirable attributes described herein. Without limiting the scope of the appended claims, the description below describes some prominent features.

In some aspects, the techniques described herein relate to a wrapped radioactive seed including: a shielded wrapper including a substantially cylindrically shaped apparatus having a shielding layer including a high-z material embedded therein, wherein the shielded wrapper includes a central longitudinal cavity and a longitudinal opening to the cavity, a substantially cylindrical radioactive seed positioned within the central longitudinal cavity, wherein the longitudinal opening is sized to allow the radioactive seed to be moved within the central longitudinal cavity that has an inner diameter that is substantially the same as an outer diameter of the radioactive seed, wherein the shielding layer within the shielded wrapper is configured to shield radiation emitted from the radioactive seed.

In some aspects, the techniques described herein relate to a shielding apparatus including: a shielding layer including a high-z material configured to shield radiation emitted by a radiation source; wherein the shielding apparatus is configured to attach to the radiation source via snap fit or friction fit to cover at least a portion of an exterior surface of the radiation source; wherein when the shielding apparatus is attached to the radiation source, the shielding layer is configured to shield radiation emitted from the radiation source.

In some aspects, the techniques described herein relate to a shielding apparatus, wherein the shielding apparatus is cylindrically shaped with a hollow interior region and the radiation source is substantially cylindrical such that the shielding apparatus receives the cylindrical radiation source in the hollow interior region.

In some aspects, the techniques described herein relate to a shielding apparatus, further including one or more protrusions configured to increase a rotational inertia of the shielding apparatus to prevent the shielding apparatus from rotating relative to a carrier in which the shielding apparatus is placed.

In some aspects, the techniques described herein relate to a shielding apparatus, wherein the one or more protrusions are visible from an exterior of the carrier in which the shielding apparatus is placed to indicate a direction in which radiation emitted from a radiation source will be shielded by the shielding layer.

In some aspects, the techniques described herein relate to a shielding apparatus, wherein the shielding layer includes electroplated gold or tantalum.

In some aspects, the techniques described herein relate to a shielding apparatus, wherein the shielding layer includes a plurality of individual, discrete layers of one or more high Z materials.

In some aspects, the techniques described herein relate to a shielding apparatus, wherein the shielding layer is embedded in an interior region of the shielding apparatus.

In some aspects, the techniques described herein relate to a shielding apparatus, wherein the shielding layer is positioned on an exterior surface of the shielding apparatus.

In some aspects, the techniques described herein relate to a shielding apparatus, wherein the shielding layer has a half value layer (HVL) of two.

In some aspects, the techniques described herein relate to a shielding apparatus, wherein the shielding layer is configured to reduce a magnitude of radiation travelling from the radiation source in the direction of the shielding layer by four times.

In some aspects, the techniques described herein relate to a shielding apparatus, further including a cap at an end portion of the shielding apparatus,
wherein the cap includes a high Z material configured to shield radiation emitted by the radiation source in the direction of the cap.

In some aspects, the techniques described herein relate to a shielding apparatus, wherein the shielding apparatus is cylindrically shaped with a hollow interior region and configured to receive a cylindrical radiation source in the hollow interior region, wherein the shielding apparatus has a thickness of between about 0.18 mm and 0.22 mm and the shielding layer has a thickness of between about 0.026 mm and 0.036 mm. In some embodiments, the shielding layers has a thickness of between about 0.01 mm to 0.06 mm.

In some aspects, the techniques described herein relate to a shielding apparatus, wherein the shielding apparatus includes plastic or polymer.

In some aspects, the techniques described herein relate to a carrier system for delivering directional radiation treatment in a tissue site according to a dosimetric plan, the carrier system including: a carrier configured to hold one or more radioactive seeds wherein the carrier includes a biocompatible material; a plurality of shielding apparatuses configured to secure to the radioactive seeds to shield a portion of radiation emitted from the radioactive seeds, wherein the plurality of shielding apparatuses each partially surround a circumference of a corresponding radioactive seed providing shielding of radiation; wherein the shielding apparatuses are secured to corresponding radioactive seeds to position the shielding layers relative to the radioactive seeds and the carrier to shield a portion of radiation emitted from the radioactive seeds in a direction relative to the carrier; and one or more connectors configured to secure to the plurality of shielding apparatuses to linearly connect the shielding apparatus.

In some aspects, the techniques described herein relate to a system, wherein the radioactive seeds and shielding apparatuses are embedded entirely within the carrier.

In some aspects, the techniques described herein relate to a system, wherein the radioactive seeds are embedded entirely within the carrier and wherein the shielding apparatuses are configured to secure to an exterior surface of the carrier.

In some aspects, the techniques described herein relate to a system, wherein the plurality of shielding apparatuses include protrusions configure to penetrate the carrier to secure the shielding apparatuses to the carrier.

In some aspects, the techniques described herein relate to a system, wherein the plurality of shielding apparatuses include one or more protrusions configured to increase a rotational inertia to reduce rotation relative to the carrier.

In some aspects, the techniques described herein relate to a system, wherein the one or more protrusions are visible from an exterior of the carrier to indicate a direction in which radiation emitted from the radioactive seeds will be shielded by the shielding layer.

In some aspects, the techniques described herein relate to a system, wherein the shielding layer includes electroplated gold or tantalum.

In some aspects, the techniques described herein relate to a system, wherein the shielding layer includes a plurality of individual, discrete layers of one or more high Z materials.

In some aspects, the techniques described herein relate to a system, wherein the shielding layer is embedded in an interior region of the shielding apparatus.

In some aspects, the techniques described herein relate to a system, wherein the shielding layer is positioned on an exterior surface of the shielding apparatus.

In some aspects, the techniques described herein relate to a system, wherein the shielding layer has a half value layer (HVL) of two.

In some aspects, the techniques described herein relate to a system, wherein the shielding layer is configured to reduce a magnitude of radiation travelling from the radioactive seed in the direction of the shielding layer by four times.

In some aspects, the techniques described herein relate to a system, further including a cap at an end portion of the shielding apparatus, wherein the cap includes with high Z material configured to shield radiation emitted by the radiation source in the direction of the cap.

In some aspects, the techniques described herein relate to a system, wherein the one or more connectors are cylindrically shaped and have a diameter of 0.5 mm.

In some aspects, the techniques described herein relate to a system, wherein the one or more connectors are configured to bend and configured to withstand compression and torsion forces to prevent stretching, compressing and twisting.

In some aspects, the techniques described herein relate to a system, wherein the one or more connectors include ribs to facilitate bending of the connector.

In some aspects, the techniques described herein relate to a system, wherein the one or more connectors include sensors.

In some aspects, the techniques described herein relate to a system, wherein the one or more connectors include therapeutic agents.

In some aspects, the techniques described herein relate to a system, wherein the one or more connectors include a high Z material.

In some aspects, the techniques described herein relate to a carrier system, wherein at least one of the one or more connectors include one or more protrusions visible from an exterior of the carrier to indicate a direction in which radiation emitted from the radioactive seed is shielded by the shielding layer.

In some aspects, the techniques described herein relate to a carrier system, wherein an end of at least one of the plurality of shielding apparatuses is flush with a surface of the carrier.

In some aspects, the techniques described herein relate to a carrier system, wherein an end of at least one of the one or more connectors is flush with a surface of the carrier.

In some aspects, the techniques described herein relate to a system, wherein the carrier includes collagen.

In some aspects, the techniques described herein relate to a shielding apparatus including: a shielding layer including a high-z material configured to shield radiation emitted by a radiation source from within a carrier; one or more fasteners protruding from a surface of the shielding apparatus and configured to protrude a depth into the carrier to secure the shielding apparatus to the carrier; wherein the shielding apparatus is configured to attach to the carrier, via the fasteners, to cover at least a portion of an exterior surface of the carrier; wherein when the shielding apparatus is attached to the carrier, the shielding layer is configured to shield radiation emitted from the radiation source within the carrier.

In some aspects, the techniques described herein relate to a shielding apparatus, wherein the shielding apparatus is spherically shaped with a hollow interior region and the carrier is substantially spherical such that the shielding apparatus receives the carrier in the hollow interior region.

In some aspects, the techniques described herein relate to a shielding apparatus, wherein the shielding apparatus is planar and the carrier is substantially rectangular cuboid, and wherein the shielding apparatus is configured to attach to a substantially planar surface of the carrier.

Details of one or more embodiments of the subject matter described in this specification are set forth in the accompanying drawings and the description below. Other features, aspects, and advantages will become apparent from the description, the drawings, and the claims. Note that relative dimensions of the following figures may not be drawn to scale.

BRIEF DESCRIPTION OF THE DRAWINGS

FIGS. 6E-6G illustrate example embodiments of wrappers on various carriers.

DETAILED DESCRIPTION

Overview

Figure 1A:
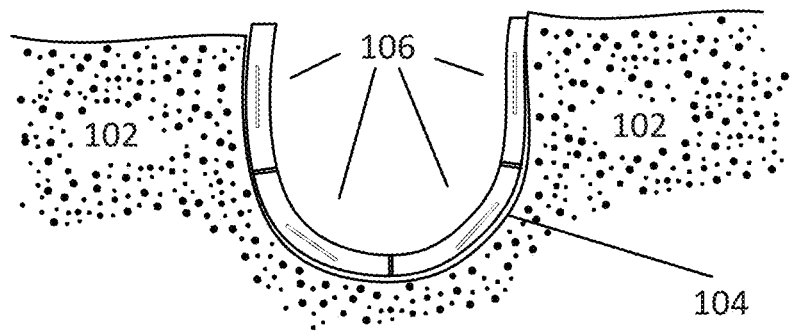
FIGS. 1A, 1B, and 1C are cross-sectional drawings illustrating a portion of patient tissue having radioactive carriers placed thereon.

Tumors are difficult to eradicate surgically as their infiltrative nature often precludes microscopically complete resection without undue morbidity or mortality. This local persistence of tumor cells may be controlled if sufficient radiation can be delivered safely prior to regrowth and replication of the residual tumor cells. Debulking surgery, followed by radiation therapy may be used for local control of a tumor. Discussed herein are various systems, methods, and devices for use in conjunction with radiation therapy, such as to deliver (and to control delivery of) radiation to a post-operative tumor bed.

Terms

To facilitate an understanding of the systems and methods discussed herein, several terms are described below. These terms, as well as other terms used herein, should be construed to include the provided descriptions, the ordinary and customary meanings of the terms, and/or any other implied meaning for the respective terms, wherein such construction is consistent with context of the term. Thus, the descriptions below do not limit the meaning of these terms, but only provide example descriptions.

Tumor: an abnormal growth of tissue resulting from uncontrolled, progressive multiplication of cells. Tumors can be benign or malignant.

Tumor bed: an anatomical area of a patient (e.g., a human or other mammal) where a tumor exists (pre-operative tumor bed) and/or an area surrounding a surgically removed tumor (post-operative tumor bed), such as a cranial cavity from which a tumor was surgically removed. Even after surgical removal of a tumor, the remaining tumor bed of the patient may include tumor cells.

Treatment area: an anatomical area that is targeted for delivery of radiation, such as from one or more radiation delivery devices (e.g., the carriers discussed below). A treatment area may include tissue below and/or around a location where the radiation deliver device is positioned, such as an anatomical area of a tumor or a tumor bed.

Treatment surface: an anatomical surface of a patient (e.g., a human or other mammal) where a radiation delivery device is to be placed to deliver radiation to a treatment area, such as the treatment surface itself and/or tissue below the treatment surface. A treatment surface may be a portion of a tumor bed or any other anatomical surface. For example, if a tumor bed is surgically created, the treatment surface may include an entire exposed surface of the tumor bed, a portion of such exposed surface, or the entire exposed surface of the tumor bed as well as a surrounding area of tissue.

Brachytherapy: radiation treatment in which the radiation delivery device is placed directly on and/or close to a treatment surface of the body, such as directly on the surface of the body, within the body, or in a tumor bed. For example, brachytherapy may be intracavitary, such as in cranial or gynecologic malignancies; intraluminal, such as in esophageal or lung cancers; external, such as in cancers of the skin; and/or interstitial, such as in treatment of various central nervous system tumors as well as extracranial tumors of the head, neck, lung, soft tissue, gynecologic sites, rectum, liver, prostate, and penis.

Seed: a radioactive material that is configured for delivery of radiation to a tumor and/or tumor bed. A seed may be in various shapes and sizes, such as cylinder, cone, sphere, pyramid, cube, prism, rectangular prism, triangular prism, and/or any combination of these or other shapes. While seeds are generally referred to herein as cylindrical, any other shape or size of seed may alternatively be used in the various systems and methods discussed herein. Seeds may comprise any combination of one or more of multiple radioactive components, such as Cs 131, Ir 192, I125, Pd 103, for example. Seeds may include a protective outer shell that partially or fully encases the radioactive material. Seeds are one form of radiation source. The term "radiation source," as used herein, generally refers to a radioactive seed (or other object that emits radiation), either alone (e.g., a seed) or embedded, or otherwise attached to, a carrier (e.g., a tile carrier with an embedded radioactive seed).

Carrier: a substrate that holds or contains a radioactive seed. A carrier that contains one or more seeds is a radiation delivery device. Carriers may comprise various materials, such as one or more biocompatible and/or bioresorbable materials, such as collagen. Thus, these bioresorbable materials are biodegradable, or naturally absorbed into the mammalian tissue over time, such as over a period of weeks or months. Carriers may be configured for permanent implantation into a tumor bed, such as to provide radioactive energy to a treatment surface surrounding an area where a tumor has been removed in order to treat any remaining malignant tissue. Carriers can be composed of various materials and take on various shapes and sizes. Examples carriers, such as carriers having various sizes, shapes, configurations, etc., are included in the following patents and patent applications, each of which is hereby incorporated by reference in its entirety and for all purposes:

U.S. patent application Ser. No. 14/322,785, filed Jul. 2, 2014, now U.S. Pat. No. 8,876,684, entitled "Dosimetrically Customizable Brachytherapy Carriers and Methods Thereof In The Treatment Of Tumors," and U.S. patent application Ser. No. 14/216,723, filed Mar. 17, 2014, now U.S. Pat. No. 9,492,683, entitled "Dosimetrically Customizable Brachytherapy Carriers and Methods Thereof In The Treatment Of Tumors."

U.S. patent application Ser. No. 14/322,785, filed Jul. 2, 2014, now U.S. Pat. No. 8,876,684, entitled "Dosimetrically Customizable Brachytherapy Carriers and Methods Thereof In The Treatment Of Tumors," and U.S. patent application Ser. No. 14/216,723, filed Mar. 17, 2014, now U.S. Pat. No. 9,492,683, entitled "Dosimetrically Customizable Brachytherapy Carriers and Methods Thereof In The Treatment Of Tumors."

Tile Carrier (also referred to as "Tile"): type of carrier that is substantially planar and generally maintains a two-dimensional planar geometry when placed in a tumor bed. Depending on the material of the tile, though, the tile may be malleable such that the tile can be deformed by bending in order to better conform to a tumor bed. For example, for tiles comprising essentially collagen (and/or other malleable materials), the tiles may be substantially bent as placed in or on a treatment surface (and/or when pressed against the treatment surface) to conform with the shape of the treatment surface, such as a post-operative tumor bed.

Custom Carrier: a carrier having one or more non-planar surfaces, such as a spherical shape or having a spherical portion. Examples of custom carriers include Spherical Carriers, Gore Carriers, and Star Carriers, noted below, as well as other custom carriers discussed herein.

Spherical Carrier (or "GammaSphere"): a substantially radially symmetrical body around an axis. A spherical carrier may also include a non-spherical portion, such as a tapered portion that extends from a spherical portion. Examples of other variations of spherical carriers is discussed in Co-pending provisional application No. 63/163,583, filed Mar. 19, 2021 and entitled "Custom Brachytherapy Carriers," which is incorporated by reference in its entirety and for all purposes.

Gore Carrier (also referred to as "Gore"): type of carrier that is 3-dimensional and conforms to the tumor bed while maintaining the geometry necessary for an effective implant. In some embodiments, gores are initially planar and are reconfigured to take on a 3-dimensional shape, such as to form a hemispherical surface that may be placed into a similarly shaped tumor cavity. Gore Carriers are further discussed in U.S. Pat. No. 8,876,684, entitled "Dosimetrically customizable brachytherapy carriers and methods thereof in the treatment of tumors," filed on Jul. 2, 2014 as application Ser. No. 14/322,785, which is hereby incorporated by reference in its entirety and for all purposes.

Star Carrier (also referred to as "Star" or "arm-based carrier"): type of carrier that assumes a conformable 3-dimensional shape when arranged and placed into an operative cavity or similar space and conforms to the treatment environment while maintaining the geometry necessary for an effective implant. However, in some embodiments, Star carriers may be used in their initial planar state to cover a relatively flat tumor or tumor bed area. Star carriers are further discussed in U.S. Pat. No. 9,492,683, entitled "Dosimetrically customizable brachytherapy carriers and methods thereof in the treatment of tumors," filed on Mar. 17, 2014 as application Ser. No. 14/216,723, which is hereby incorporated by reference in its entirety and for all purposes.

Loader: a device that aids in placement of radioactive seeds in carriers, such as via injection of seeds into carriers. A loader, also referred to herein as a "loading device," may include multiple components, such as to hold a carrier in place and guide a delivery device (e.g., a needle or injector) into the carrier in order to place a seed at a precise location in the carrier. The "Loader Patents" refers to U.S. patent application Ser. No. 13/460,809, filed Apr. 30, 2012, now U.S. Pat. No. 8,939,881, entitled "Apparatus For Loading Dosimetrically Customizable Brachytherapy Carriers," and U.S. patent application Ser. No. 14/696,293, filed Apr. 24, 2015, entitled "Apparatus and Method for Loading Radioactive Seeds Into Carriers," which are each hereby incorporated by reference in their entirety for all purposes, describe several embodiments of loaders. As discussed further herein, loaders may be operated manually, such as by human operators, or may be fully automated, such that carriers can be loaded with seeds using an automated process. Alternatively, loaders may be configured to be automated in part and require manual operation in part.

High Z Materials: any element with an atomic number greater than 20, or an alloy containing such materials.

Hot Carrier: a carrier that is loaded with a material that is radioactive.

Cold Carrier: a carrier that is not loaded with a material that is radioactive, such as a carrier prior to loading of a radioactive seed.

Shielding Material: any material that restricts movement of radioactive particles, such as by absorbing, reflecting, and/or scattering radioactive particles. The term "shielding," as used herein, generally refers to any mechanism of preventing radiation from moving through and exiting a corresponding shielding material, such as by the shielding material absorbing, reflecting, or otherwise blocking the radiation. Shielding materials in various forms may be used in the various embodiments discussed herein. For example, a shielding material may be in the form of a particle, wire, rod, cylinder, bar, sheet, liquid, solution, foam, or any other form in which a material having radiation absorbing and/or reflecting properties is possible. A shielding material provides a shielding rate, which is generally an amount of shielding of radioactive energy (that is emitted from one or more radiation sources), provided by the particular shielding materials. Similarly, a shielding layer comprising multiple shielding materials and an isolation sheet have associated shielding rates, which are dependent on the combination of shielding (and possibly non-shielding) materials therein. For some applications, such as based on clinical need, an isolation sheet that provides a shielding rate of 25%, 50%, 75%, 90%, 95%, 98%, or some other shielding percentage, may be desired. As discussed herein, material composition, shape, size, dimensions, etc. may impact the shielding abilities of a shielding material. For applications (e.g., based on clinical need) where a higher shielding percentage is desired than may be provided by a single shielding material, multiple shielding materials may be used in combination, in one or more shielding layers or isolation sheets.

In some embodiments, shielding materials comprise high Z materials, such as tantalum, gold, platinum, tin, steel, copper, aluminum, etc. (e.g., a 0.01 mm to 0.06 mm thickness metallic foil). In other embodiments, any other material that reduces penetration of radiation may be a shielding material. For example, a non-metallic, yet dense compound, may be used alone (or in combination with a metallic material) as a shielding material. Such a non-metallic shielding material may advantageously lessen the chance of 1) MRI artifacts, 2) deflection of the isolation sheet, and/or 3) MRI-induced heating, such as may be caused by current loop induction and/or radio-frequency induced tissue heating that may be caused by metallic shielding materials. Depending on the particular non-metallic material, thickness of the material may be larger than a required thickness of a metallic shielding material, in view of the general enhanced shielding abilities of metallic materials. Non-metallic high density shielding materials may beneficially provide shielding of non-target tissues from radiation particularly in applications where MRI or other magnetic field exposure may be anticipated. Examples of non-metallic shielding materials include polyetheretherketone (PEEK), nanoparticles, polymeric nanoparticles, encapsulated nanoparticles, calcium carbonate, calcium phosphate, calcium sulfate, barium sulfate, zirconium dioxide, polymers and polymer hybrids of these and other materials. Shielding materials may be combined to form a composite shielding material. For example, a metallic cylinder may be filled with (non-metallic) liquid calcium carbonate, in order to form a shielding material that better addresses one or more of the clinical needs of the patient than a separate metallic cylinder and liquid calcium carbonate or a solid metallic rod.

Any reference herein to a shielding material, even if the example references a particular metallic or non-metallic material (e.g., a particular form of a particular material), could be implemented with any other shielding material (e.g., a different form and/or different material) and/or combination of shielding materials. For example, a golden rod shielding material can be replaced with a PEEK mesh shielding material that provides similar radiation absorption and/or reflecting properties. Dimensions (e.g., width, height, radius, thickness, etc.) of various shielding materials that provide the same radiation absorption and/or reflective properties may vary from one material to another.

Shielding Layer: one or more shielding materials configured for placement on or near radioactive sources (e.g., seeds) for reducing penetration of radiation outside of a treatment area. A shielding layer may comprise discrete layers of one or more materials, such as a gold foil sheet or a polymer sheet. In other embodiments, a shielding layer may include particles of high Z or non-metallic material that may be embedded within a shielding layer substrate (comprising a shielding layer material), such as a wrapper. In some embodiments, the shielding layer may be perforated or include a grid or mesh pattern, for example, interwoven with one or more high Z materials. A perforated or mesh shielding layer may improve effectiveness of the isolation sheet, for example, by configuring the shielding layer with desired radioactive shielding properties. A perforated or mesh shielding layer may also improve ease of handling (e.g., malleability that allows placement in the treatment area in the desired configuration) and/or imaging characteristics (e.g., reduces artifacts from shielding materials).

Wrapper: an apparatus configured for placement on or near, or attachment to, radioactive sources (e.g., seeds). A wrapper may include one or more shielding layers that is configured to shield (e.g., to block, absorb, and/or absorb) a portion of the radiation emitted from the radioactive seed, such as from 5%-95% of radiation. A wrapper may be generally cylindrical in shape, with at least a portion of the cylindrical shape open such that a central axis of the cylinder is viewable from outside the wrapper. For example, a wrapper may be cylindrical with a longitudinal slit missing along a length of the cylinder. For example, the wrapper may be a semicircular cylinder with 180 degrees of the circumference comprising the shielding layers and the opposing 180 degrees being open. Thus, a wrapper may define a cavity (e.g., the inner cavity of the cylinder) configured to receive a radioactive seed. In some embodiments, the inner cavity of the wrapper, or portions thereof, may be generally cylindrical or any other shape as required or desired to match a shape of a seed to receive the seed. For example, the inner cavity of the wrapper may be shaped to receive a cylindrical seed or a spherical seed or a rectangular cuboid seed.

In some embodiments, a wrapper may be configured for placement on or attachment to a carrier, without direct coupling to a radioactive seed. For example, a "carrier wrapper" may be placed and/or replaced on a surface of a carrier during a medical procedure, for example, by a medical professional to provide shielding from radiation from one or more radioactive seeds embedded in the carrier. In various implementations, a carrier wrapper may cover a portion of a carrier surface, all of a carrier surface, or multiple carrier surfaces. A carrier wrapper may secure to a carrier by adhesion, for example, by adhesive properties of the wrapper and/or carrier. A carrier wrapper may secure to a carrier by one or more fasteners of the wrapper configured to pierce the carrier to anchor the wrapper to the carrier. A carrier wrapper may be shaped to fit to a shape and/or size of a carrier. For example, a carrier wrapper configured for placement on a top surface of a tile carrier may be generally planar and sized to match the top surface size. In another example, a carrier wrapper configured for placement on a spherical surface of a carrier (e.g., a top surface of a spherical carrier) may be generally spherical with an inner cavity configured to receive the spherical surface of the carrier, such that the wrapper fits on or around the spherical surface.

A radioactive seed coupled to a wrapper is generally referred to as a "wrapped radioactive seed." A radioactive seed may be attached to a wrapper via a friction fit and/or snap fit assembly. For example, a wrapper may be flexible enough to expand a diameter of the inner cavity to allow a radioactive seed to be inserted into the inner cavity. The seed in the cavity may then be held in place via a snap fit or friction fit between the wrapper and the radioactive seed. For example, a snap fit may be realized via one or more protrusions or other mechanical features at the edge of the wrapper that extend into the inner cavity. In general, the term "radioactive seed" or "seed" herein may refer to either a radioactive seed as described above and/or a wrapped radioactive seed.

A wrapped radioactive seed may be attached or embedded within a carrier for placement adjacent a treatment surface of a patient for delivery of radioactive therapy, or a wrapped radioactive seed may be placed directly on a treatment surface without attachment to a carrier.

Wrappers may comprise one or more materials such as plastics, polymers or other bio-compatible material, embedded with one or more shielding materials. Alternatively, a wrapper may be entirely composed of a shielding material. A wrapper may comprise a single continuous material or may comprise discrete layers of materials. In some embodiments, a wrapper may not include shielding material and may be used to hold a seed, for example, to facilitate loading a seed in a carrier. With a radioactive seed positioned within the cavity of a wrapper, radiation emitted from the seed is shielded in directions of the shielding material of the wrapper, while radiation may exit the seed and/or wrapper in directions that do not include a shielding material (e.g., the cavity opening of the wrapper) into patient tissue for adjuvant therapy.

Wrappers may be customized for a particular patient and/or treatment plan. For example, the opening of a wrapper may be adjusted to provide a reduced or increased area of radiation delivery from the wrapped radioactive seed.

Shielding Specifications (also referred to as a "Shielding plan"): attributes of one or more wrapped radioactive seeds, such as attributes of shielding layers and any other layers (e.g., collagen or other spacing layer, adhesive layers, etc.) included in the wrappers, such as any combination of those attributes (also referred to herein as "characteristics") of wrapper shape, size, cavity dimensions, shielding material(s), shielding layer(s), and/or other aspects. Shielding specifications may be in digital form (e.g., in an electronic data structure, such as a database or table), written form (handwritten by an oncologist or surgeon or printed from a digital form), and/or may be developed and/or updated without (or prior to) placement of the wrapped radioactive seeds. Thus, shielding specifications may be developed in real-time based on clinical need and/or other patient characteristics.

Shielding specifications may be determined to best meet one or more of many clinical needs (and/or other shielding goals or requirements), such as to provide shielding that:

results in a directional therapeutic treatment area. Radiation sources, such as carriers embedded with radioactive seeds, generally emit radiation in an omnidirectional manner, such that all areas around the radiation sources absorb radiation (possibly in varying amounts depending on the shape, size, placement, etc. of the radiation source). Shielding specifications may include use of wrapped radioactive seeds that reduce the range of radiation by blocking radiation emitted in certain directions;

reduce risk of imaging distortion due to interference by the shielding materials (or other components);

reduce risk of RF heating caused by energy from MRI or other imaging devices, thereby reducing risk of further patient injuries, such as burning, as a result of imaging;

provide a preferred (or required in some embodiments) shape, size, etc., of wrappers, such as to allow placement of wrapped radioactive seeds in irregularly shaped treatment areas; and/or reduce risk of deflection (e.g., movement) of shielding materials within the wrappers by energy from imaging devices, such as MRI.

Dosimetry: a process of measurement and quantitative description of the radiation absorbed dose (e.g., rad) in a tissue or organ.

Dosimetric Plan: a description of the prescribed dosimetry, such as for a particular patient, associated with a particular clinical condition, and/or for use in a particular surgical cavity, etc. For example, a dosimetric plan may indicate position, quantity, radioactive strength, etc., for placement of radioactive carriers on a treatment surface of a patient, such as in view of characteristics of a tumor removed (or planned for removal) from the patient. In some embodiments, dosimetric plans may include shielding specifications (or a "shielding plan), such as characteristics of one or more wrappers that are used in conjunction with radioactive seeds (e.g., as wrapped radioactive seeds) in accordance with the dosimetric plan. In other embodiments, the dosimetric plan for a patient may not include shielding specifications and, for example, may leave determination of the shielding specifications to another specialist, such as a surgeon that implements the dosimetric plan. Thus, the shielding specifications may be determined based on clinical need, even in real-time as or after some of the prescribed radioactive carriers are positioned on the treatment surface. Determining shielding specifications based on clinical need may better accommodate actual clinical condition of a patient that may be unknown and/or change after creation of a dosimetric plan, such as after removal of a tumor. In some embodiments, clinical need may be considered in order to increase shielding around sensitive tissue areas (e.g., an optic nerve, vital organs, etc.) or scar tissue areas. Any discussion herein of determining shielding specifications according to a dosimetric plan, which is one type of "treatment plan" specific to radiation therapy planning, refer additionally to determination of those same shielding specifications according to clinical need, such that shielding specifications may be determined based on a dosimetric plan and/or clinical need.

Therapeutic Index: relationship between an amount of therapeutic effect provided by a therapeutic agent, such as one or more radioactive seeds in carriers, to an amount that causes toxicity. The therapeutic index may indicate a relative amount of healthy tissue (non-target tissue) receiving radiation (e.g., above a certain dosage level) compared to an amount of the target area (e.g., a tumor or tumor bed) receiving radiation. The therapeutic index may be a ratio of radiation delivered to a treatment area (e.g., tumor or tumor bed) to radiation delivered to areas surrounding the treatment area. Thus, a higher therapeutic index generally indicates better localization of radiation to the treatment area, sparing as much of the surrounding area from radiation as possible. Accordingly, improving the therapeutic index may increase local control of tumors and/or decrease the morbidity of treatment.

Example Carrier Embodiments

Figure 1B:
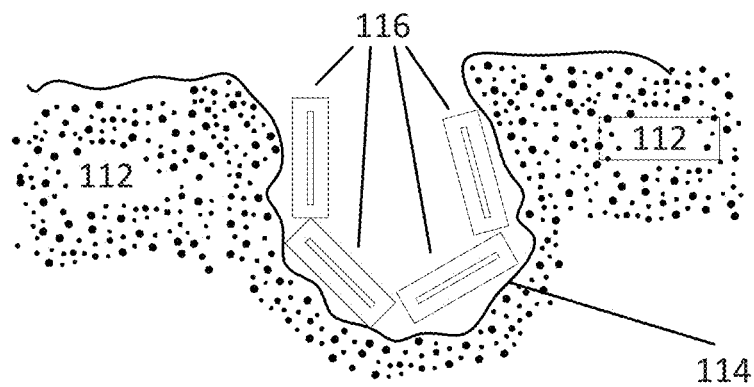

FIGS. 1A and 1B are cross-sectional drawings illustrating a portion of patient tissue 102 and 112 having tumor beds 104 and 114 therein, respectively. These tumor beds 104 and 114 may have been created by a surgical process, such as a tumor debulking process that removed tumor cells. For example, the tissue 102 or 112 may represent cranial tissue of a human (or other mammal) wherein the tumor beds 104 and 114 are surgically created in order to remove one or more tumors from the brain (and/or surrounding areas) of the patient. Thus, the tissue 102 and 112 may represent different types of material, such as bone, fatty tissue, brain tissue, etc. Any reference herein to "tissue" may reference to any type of mammalian material, including bone, fatty tissue, brain tissue, etc.

In the example of FIG. 1A, four tile carriers 106 are illustrated as already placed within the tumor bed 104. Placement of the tiles 106 in the tumor bed 104 may occur in the surgical room, such as immediately after a surgical procedure, or elsewhere at some time after the surgical procedure, such as in a separate procedure performed hours, days, or weeks later. In the embodiment of FIG. 1A, the tiles 106 are pliable such that they conform to the treatment surface, which is the non-planar outer surface of the tumor bed 104 in this example. In one embodiment, the tiles 106 may comprise collagen that provides such flexibility in conforming the tiles 106 to a nonplanar surface. In the example of FIG. 1B, tiles 116 that are placed in tumor bed 114 of tissue 112 are comprised of a non-pliable substrate, such as a polymer, that maintains its substantially planar shape even when placed within the tumor bed 114. For ease of discussion, tile carriers discussed herein are illustrated as being flexible, such as the tiles 106 in FIG. 1A. However, any other type of tile carrier, as well as other configurations of carriers, such as gore, star, or dot carriers, may be used alternatively. Thus, any discussion herein of a tile carrier or any other particular carrier should be interpreted to also include embodiments using other types of carriers, no carriers at all (e.g., radioactive seeds could be placed in a tumor bed without first being placed in a carrier), and/or any other radiation delivery device.

Figure 1C:
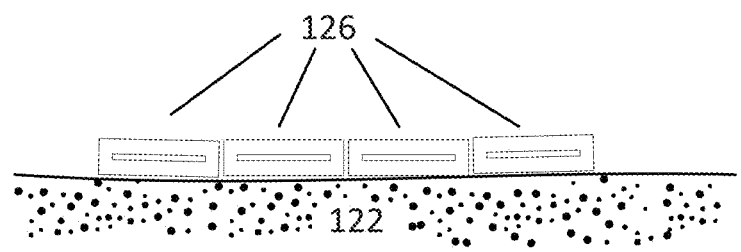

In the examples of FIGS. 1A and 1B, the tiles 106 and 116 each include a radioactive seed embedded therein. As discussed in the related patents and patent applications noted above, the radioactive seeds can have various shapes, sizes, and characteristics. In the examples discussed herein, radioactive seeds are illustrated as generally cylindrical, such as the cylinders included in each of the tiles 106 and 116 of FIGS. 1A and 1B. However, other shapes and sizes of seeds may be used in other implementations. In the examples discussed herein, radioactive seeds are substantially rigid, such that they maintain their shape within their respective carriers. Thus, as shown in FIG. 1A, even when the carriers 106 near the bottom of the tumor bed 104 are deformed to better engage with the treatment surface, the seeds therein retain their linear cylindrical shape. In other embodiments, seeds may be more pliable, such that they are somewhat malleable in taking on a shape of a specific treatment surface. In the example of FIG. 1C, a tumor cavity is not present and, thus, the carriers 126 are placed on a substantially planar treatment area of tissue 122, such as a patient's skin covering the skull or other tissue.

In the examples of FIGS. 1A, 1B, and 1C radiation is delivered to the corresponding treatment area by the radioactive seeds within the carriers 106, 116, and 126, respectively. However, radiation from these seeds may also extend to other areas of tissue that are outside of the desired treatment area. For example, radiation emitted from top surfaces of the carriers may extend to surrounding tissue outside of the treatment area, other portions of tissue that come near and/or contact the treatment surface (e.g., the hand of a patient placed over the tumor bed 104), or even tissue of another person or animal, such as a spouse that lays near the treatment surface and, thus, receives radiation from the radioactive seeds. Accordingly, depending on placement of the carriers, size and shape of treatment surface, radioactive seed intensity, and/or many other factors, the therapeutic index for use of such carriers may be unnecessarily low. Discussed herein are various shielding devices, systems, and methods, which are generally designed to improve therapeutic index for delivery of radiation using brachytherapy.

Figure 2A:
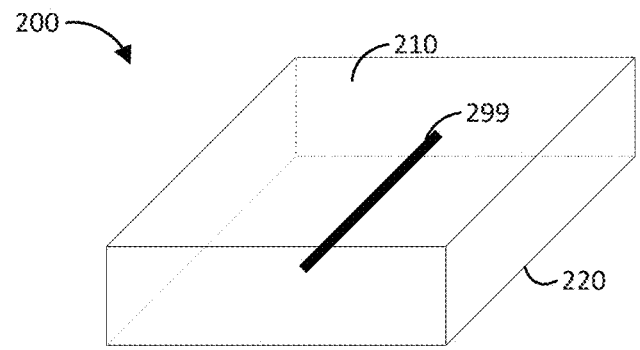
FIG. 2A shows a perspective view of an embodied carrier device in a tile form.

FIG. 2A shows a perspective view of a tile carrier 200 that serves as a loadable spacer for a radioactive seed 299. Additionally, the tile carrier 200 may include an antipodal surface 210 opposite of the treatment surface 220.

Figure 2B:
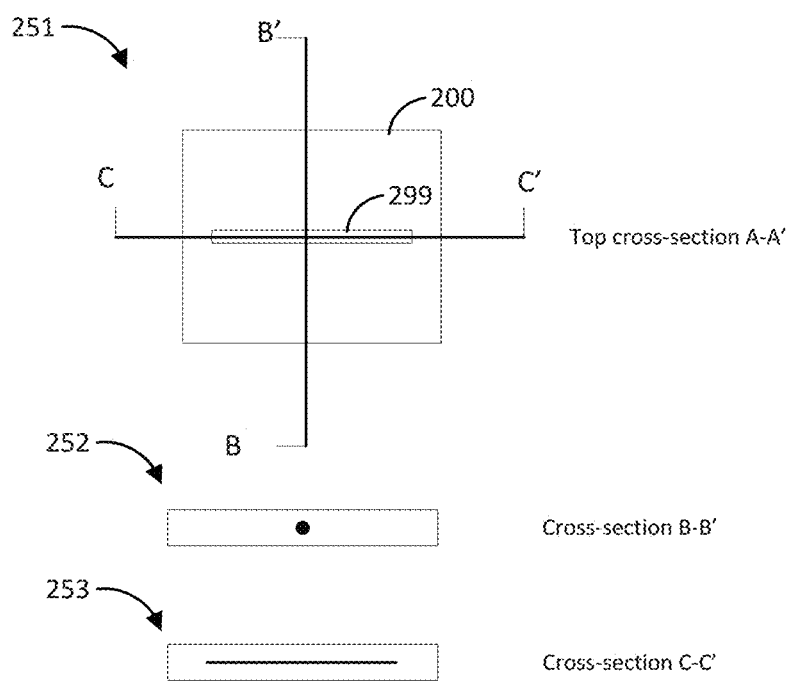
FIG. 2B illustrates cross-sectional views of an example carrier tile.

FIG. 2B illustrates cross-sectional views of an example tile carrier 200. Cross-sectional view 251 is a top view of the example tile carrier 200. Cross-sectional view 252 is a front view of the example tile carrier 200 with embedded seed 299. Cross-sectional view 253 is a side view of the example tile carrier tile 200 with embedded seed 299.

Example Wrapper Embodiments

Disclosed herein are several embodiments of wrappers, which are generally any materials that are placed over, around and/or that are included with radioactive seeds in order to provide directional radioactive shielding. As noted above, a wrapper may include a single shielding layer, which itself may include one or more shielding materials, or multiple shielding layers in various positional relationships to one another. Wrappers may improve a therapeutic index associated with a dosimetry plan. Shielding materials used in wrappers may include, for example, high-z materials or alloys thereof, in various forms, formed in shielding layers such as a foil, mesh, oriented strips, grid, embedded, sprayed, bio-adhered, or an on-lay in or on a substrate, such as one or more layers of plastic or polymer. While specific shapes, material compositions, properties, etc. are disclosed herein with reference to various example wrappers, variations on these examples are anticipated.

Figure 3A:
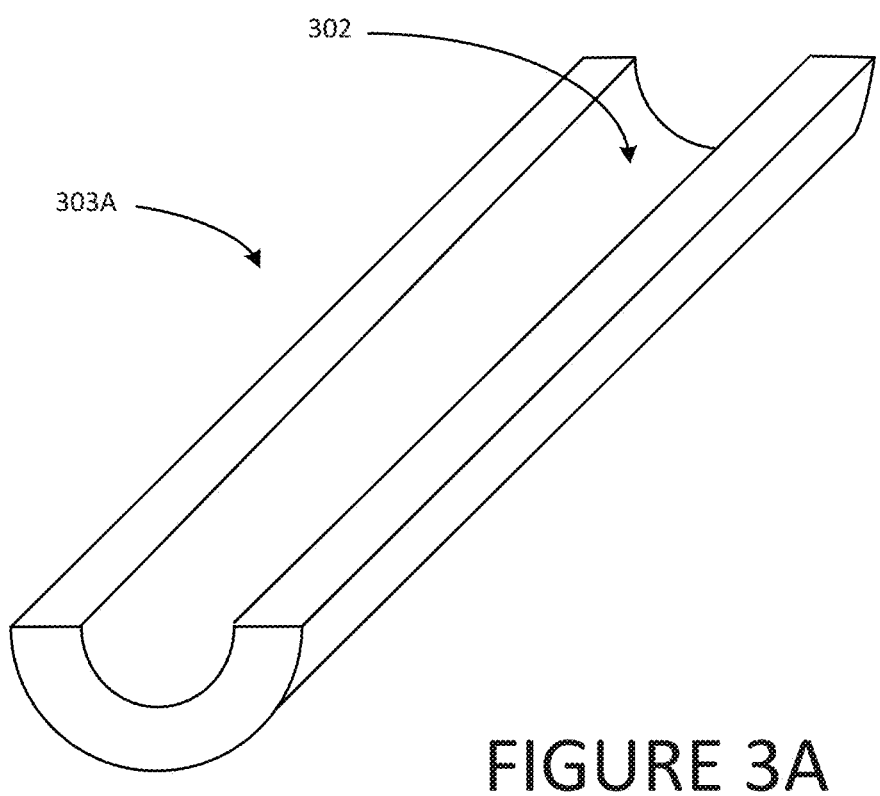
FIG. 3A is a perspective view of an example embodiment of a wrapper.

FIG. 3A is a perspective view of an example embodiment of a wrapper 303A. In the example of FIG. 3A, the wrapper 303 is generally cylindrical in shape and includes a central cavity 302 sized to fit around (and/or engage with) a cylindrical radioactive seed. For ease of description herein, wrappers are generally described as having a cylindrical shape, such as in FIG. 3A. However, any other shapes of wrappers having the same or similar characteristics are also contemplated. Thus, any discussion of features or characteristics of a wrapper of a particular shape (e.g., cylindrical with a central cavity) are also applicable to any other shape wrapper that is not specifically discussed herein. For example, other embodiments of wrappers may include a cavity that is generally cylindrical, spherical, cubical, or rectangular cuboid in shape, such as to match the shape of a seed. Other embodiments of wrappers, which may be referred to herein as "carrier wrappers," may be shaped to fit on or around a carrier or portions thereof. For example, a carrier wrapper may be generally planar for placement on a surface of a tile carrier or a wrapper may include a cavity that is generally spherical to fit on or around a spherical carrier or portions thereof, or generally rectangular cuboid in shape, such as to match the shape of a tile carrier. For ease of description, example seeds that are generally cylindrical in shape are discussed herein. However, any other shape of seed may be used in conjunction with a wrapper in a similar manner.

In some embodiments, the wrapper 303A comprises a single material, such as a single shielding material or a single non-shielding material which may, for example, be a uniform or continuous material. For example, the wrapper 303A may comprise a single plastic or polymer or other bio-compatible material or may comprise a single high Z material. In some embodiments, the wrapper 303A may comprise more than one material such as discrete layers, portions, or regions of various materials. The wrapper 303A may be manufactured by extrusion, injection molding, 3D printing or the like.

Figure 3B:
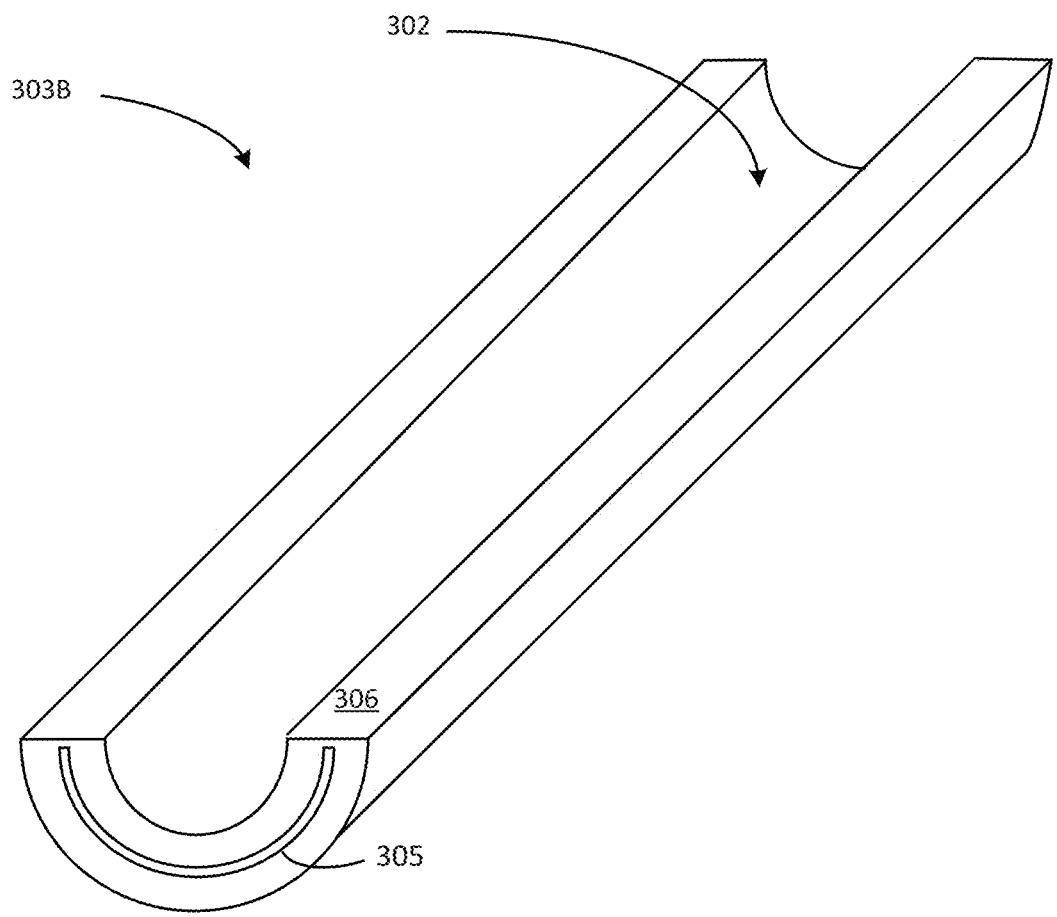
FIG. 3B is a perspective view of an example embodiment of a wrapper with a shielding layer on or around a seed.

FIG. 3B illustrates another example of a wrapper 303B that includes a shielding layer 305 embedded within a non-shielding material 306 that forms the remainder of the wrapper 303B. As discussed further herein, a shielding material may be embedded within and/or attached to a non-shielding material to form a wrapper in various configurations.

The shielding layer 305 may comprise one or more high Z materials. For example, the shielding layer 305 may include gold (Au) or tantalum (Ta). In some embodiments, the shielding layer 305 may comprise electroplated layer(s) of a high Z material such as gold. In some embodiments, a wrapper may comprise more than one shielding layer, for example, two or three discrete shielding layers which may each be positioned within the wrapper at various distances away from a seed and separated by each other by a portion, region or layer of a non-high Z material of the wrapper, such as a plastic or polymer.

In some embodiments, a shielding layer may have a variable thickness along a length and/or about a circumference of a seed. A shielding layer of variable thickness may allow radiation to be delivered at varying doses to varying regions in a tumor bed such as according to a prescribed treatment plan. In some embodiments, a shielding layer may have a thickness between about 0.01 mm and 0.06 mm, about 0.02 mm and 0.03 mm, between about 0.025 mm and 0.035 mm, between about 0.03 mm and 0.04 mm, or any other thickness. In some embodiments, the shielding layer 305 may have a thickness of about 0.026 mm or about 0.036 mm.

The thickness and/or material of the shielding layer 305 may depend on the desired dosimetric plan. For example, it may be desired that the shielding layer 305 have a certain half value layer (HVL). HVL refers to the thickness of the material at which the intensity of radiation entering it is reduced by one half. In some embodiments, the shielding layer 305 may have a HVL of 1, 1.5, 2, 2.5, 3 or any other HVL. In some embodiments, the shielding layer 305 may have a HVL of 2 such that the intensity/magnitude of the radiation entering the shielding layer 305 from a radioactive seed is reduced by 4 times before exiting the shielding layer 305. The HVL may differ depending on the material. Thus, a thicker shielding layer 305 may be required for some materials to obtain the same reduction in radiation intensity/magnitude as other materials. In some embodiments, shielding may be prescribed as a percentage of dose reduction. For example, a shielding layer may provide a dose reduction of between about 30% to 90%.

Figure 3C:
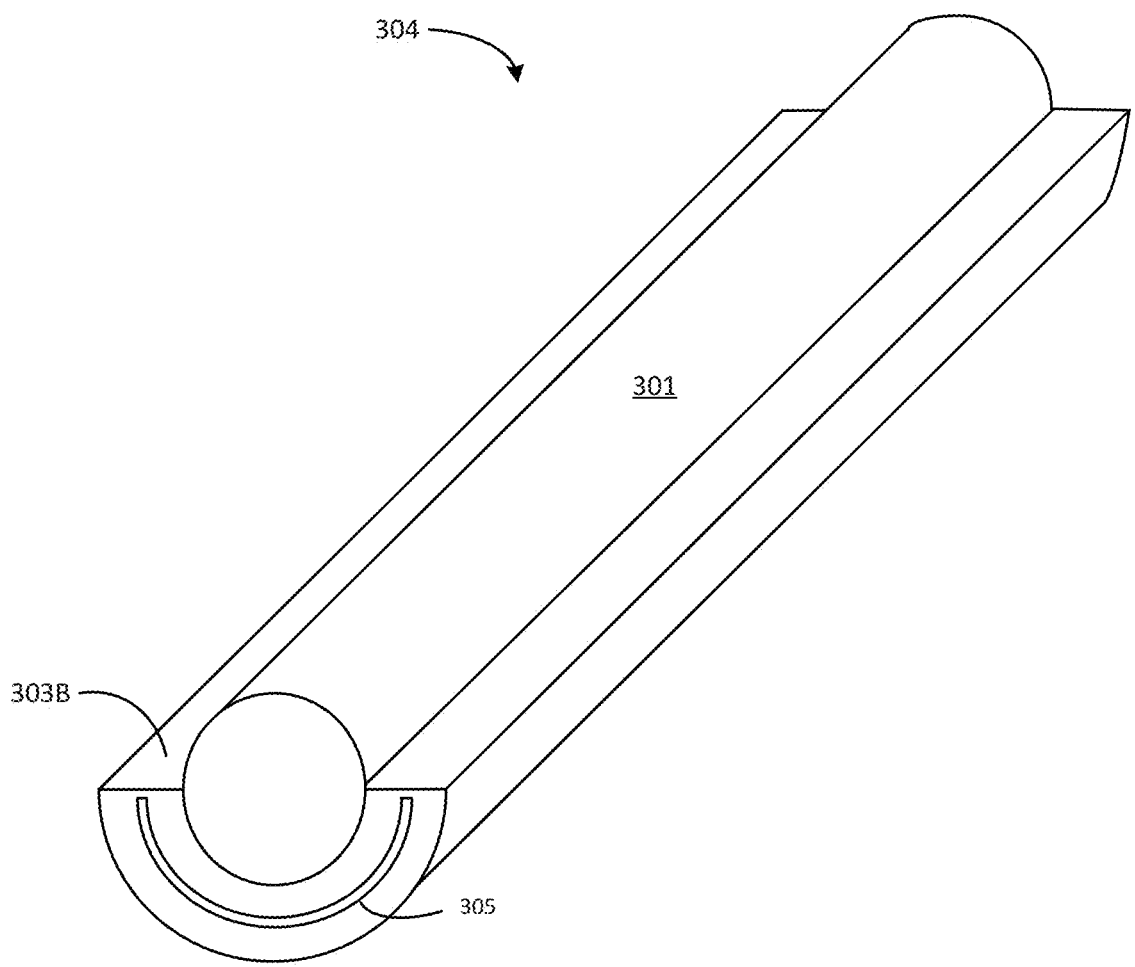
FIG. 3C is a perspective view of an example embodiment of a wrapped seed, wherein the wrapper includes a shielding layer.

FIG. 3C illustrates the wrapper 303B with a radioactive seed 301 positioned in the wrapper cavity. This combination of a wrapper and radioactive seed is referred to herein as a wrapped seed, such as wrapped seed 304. As discussed further herein, a radioactive seed may be coupled to a wrapper via various means, such as a friction fit, snap fit, and/or an adhesive.

In the embodiment of FIG. 3C, the seed 301 is rod shaped or cylindrically shaped. Depending on the embodiment, the seed 301 may have a length between about 4 mm and 5 mm or any other length as required or desired. In some embodiments, the seed 301 may have a length of 4.5 mm. The seed may have a diameter of between about 0.65 mm and 0.75 mm, between about 0.7 mm and 0.8 mm, or between about 0.75 mm and 0.85 mm. In some embodiments, the seed 301 has a diameter of about 0.7 mm, or about 0.8 mm, or about 0.9 mm.

In some embodiments, the wrapper 303 (e.g., the wrapper 303A, 303B, or any other wrapper discussed herein) may attach to the seed 301 by adhesion. For example, the wrapper 303 may include an adhesive surface and/or material on the inner surface of the cavity that adheres the seed 301 to the cavity walls of the wrapper 303. In some embodiments, the wrapper 303 may secure to the seed 301 by mechanical force. For example, the wrapper 303 may encompass a majority circumferential surface of the seed 301, for example such that the seed 301 may be force fitted or snapped into the wrapper 301.

In some embodiments, the wrapper 303 may be removably secured to the seed 301 such that the seed 301 may be inserted into the wrapper 303 or removed from the wrapper 303. The wrapper 303 may be quickly and easily applied to the seed 301, for example, by adhesion or snap fit. For example, a medical professional may place the wrapper 303 on the seed 301 during a medical procedure prior to placing the wrapped seed 304 in a tumor bed of a patient. The medical professional may place the wrapper 303 on the seed 301 according to a desired dosimetric plan or radiation dose to be delivered to the patient.

In the embodiment of FIG. 3C, the wrapper 303B has a uniform thickness along a length of the seed 301. For example, the wrapper 303B may have a thickness between about 0.1 mm and 0.2 mm, between about 0.15 mm and 0.25 mm, between about 0.2 mm and 0.3 mm, or any other thickness. In some embodiments, the wrapper 303B may have a thickness of 0.2 mm. In some embodiments, a wrapper may have a variable thickness along a length and/or about a circumference of a seed.

In some embodiments, the shielding layer 305 may be closer to or farther from the seed 301 than is shown in wrapper 303B. For example, in some embodiments, the shielding layer 305 may be positioned closer to the cavity walls of the wrapper 303B such that the shielding layer 305 is closer to the seed 301 or even in physical contact with the seed 301. As another example, in some embodiments, the shielding layer 305 may be positioned in an outer region of the wrapper 303B such that the shielding layer 305 is closer to or even exposed on an outer surface of the wrapper 303B. The shielding layer 305 may be positioned at any distance from the cavity walls of the wrapper 303B, and the distance may be uniform or variable along a length and/or about a circumference of the wrapper 303B.

Figure 3D:
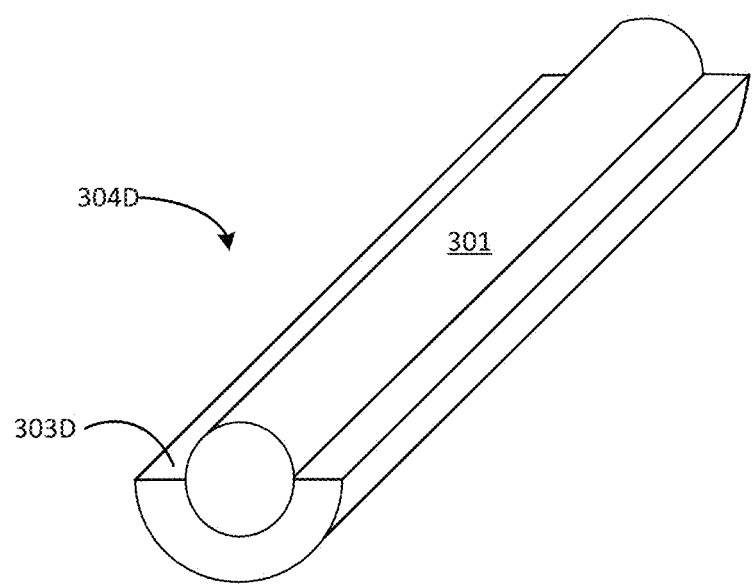
FIG. 3D is a perspective view of an example embodiment of a wrapped seed, wherein the wrapper does not include a shielding layer.

FIG. 3D is a perspective view of another example wrapped seed 304D comprising a wrapper 303D and the seed 301 positioned within a central cylindrical cavity of the wrapper 303D. In this example, wrapper 303D includes only non-high Z materials, such as plastics or polymers. The wrapper 303D may comprise a uniform, continuous non-high Z material or may comprise discrete layers, portions, or regions of various non-high Z materials. In such embodiments where the wrapper 303D does not comprise a shielding layer, the wrapper 303D may be used to facilitate placement of the seed 301 within a carrier, for example, as discussed elsewhere herein such as with reference to FIGS. 10A-10B and 11. Any of the wrapper embodiments discussed herein may be implemented with or without a shielding layer.

Figure 3E:
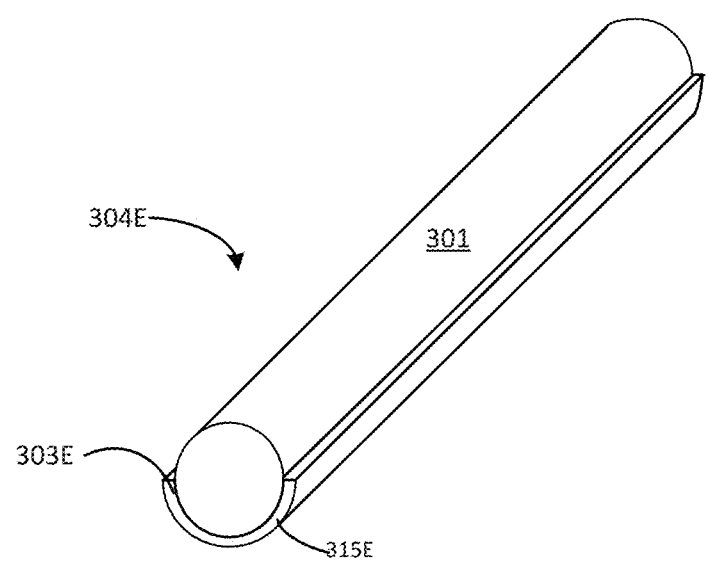
FIG. 3E is a perspective view of an example embodiment of a wrapped seed.

FIG. 3E is a perspective view of another example wrapped seed 304E comprising a wrapper 303E and the seed 301 positioned within a central cylindrical cavity of the wrapper 303E. In this embodiment, the wrapper 303E comprises only a shielding layer 315E, without a corresponding non-shielding layer. The shielding layer 315E may comprise a uniform, continuous high Z material or may comprise discrete layers, portions, or regions of various high Z materials, such as a foil having a thickness in the range of 0.01 mm to 0.06 mm. In the embodiment of FIG. 3E, the wrapper 303E (which is equivalent to the shielding layer 315E in the specific embodiment of FIG. 3E) may include an adhesive property and/or substance to facilitate adherence of the seed 301 to the cavity wall of the wrapper 303E. This may facilitate quick and simple application of the wrapper 303E, and the shielding layer 315E, to the seed 301. For example, a medical professional may place the wrapper 303E on the seed 301 during a medical procedure prior to placing the wrapped seed 304E in a tumor bed of a patient. The medical professional may place the wrapper 303E on the seed 301 according to a desired dosimetric plan or radiation dose to be delivered to the patient. Any of the embodiments of a shielding layer discussed herein may be implemented as a wrapper itself (similar to wrapper 303E) and/or in conjunction with one or more non-shielding layers and/or additional shielding layers.

Figure 3F:
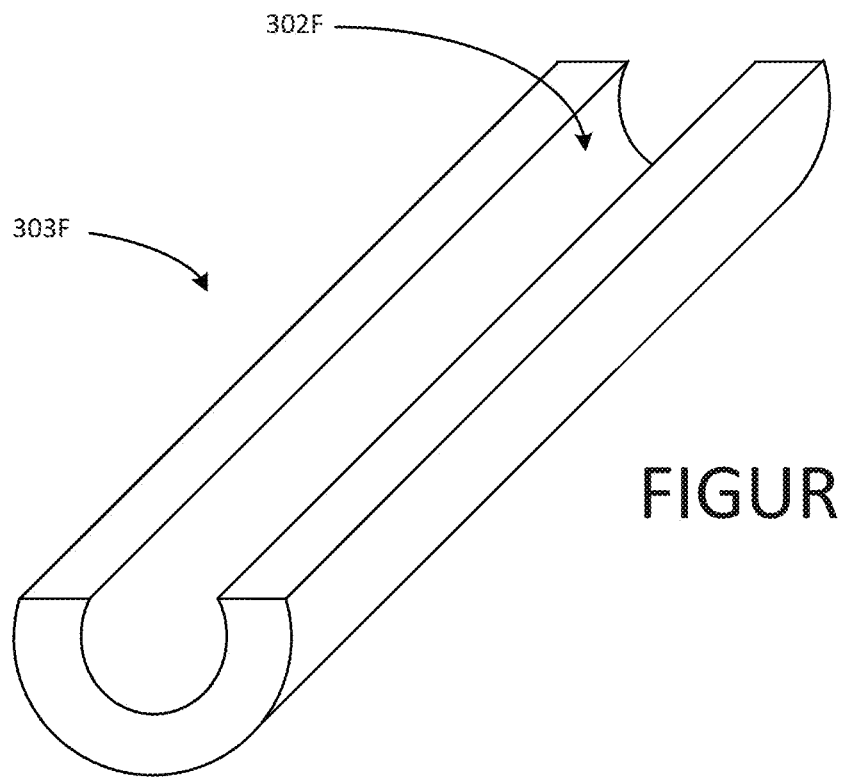
FIG. 3F is a perspective view of an example embodiment of a cylindrically shaped wrapper with more than half (e.g., more than 180 degrees) of the circumference of the cylinder intact around a cavity portion for holding a seed by snap fit.
Figure 3G:
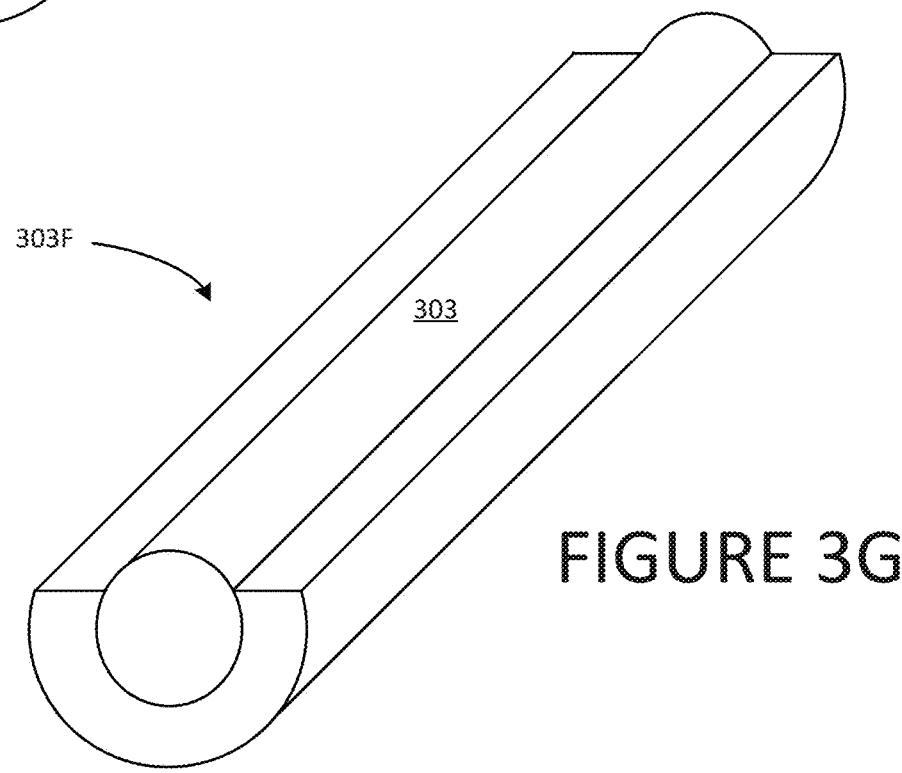
FIG. 3G is a perspective view of an example embodiment of a wrapped seed with a seed snap-fitted in the wrapper.

FIG. 3F is a perspective view of another example wrapper 303F. In this example, the wrapper 303F is cylindrically shaped, with more than half (e.g., more than 180 degrees) of the circumference of the cylinder intact. Thus, an opening to the cavity 302F is narrower than the diameter of the cavity 302F. Accordingly, a seed having an outer diameter of approximately equal to the diameter of the cavity 302F (or slightly less than the diameter of the cavity 302F) may be snapped into the cavity 302F by pressing the seed against the entrance to the cavity 302F of the wrapper 303F to slightly flex the wrapper 303F so that the seed enters the cavity 302F. Once in the cavity 302F, the seed 303F is held in place. FIG. 3G illustrates the same wrapper 303F with a radioactive seed 303 placed therein, and held in place due to the narrow entrance to the cavity 302F. Any other embodiments of wrappers discussed herein may include a similar snap-fit configuration and/or characteristic, for example, where a portion of the wrapper is flexed outward by movement of a seed towards a cavity of the wrapper until the seed snaps through an opening to a cavity of the wrapper and enters the cavity.

Figure 4A:
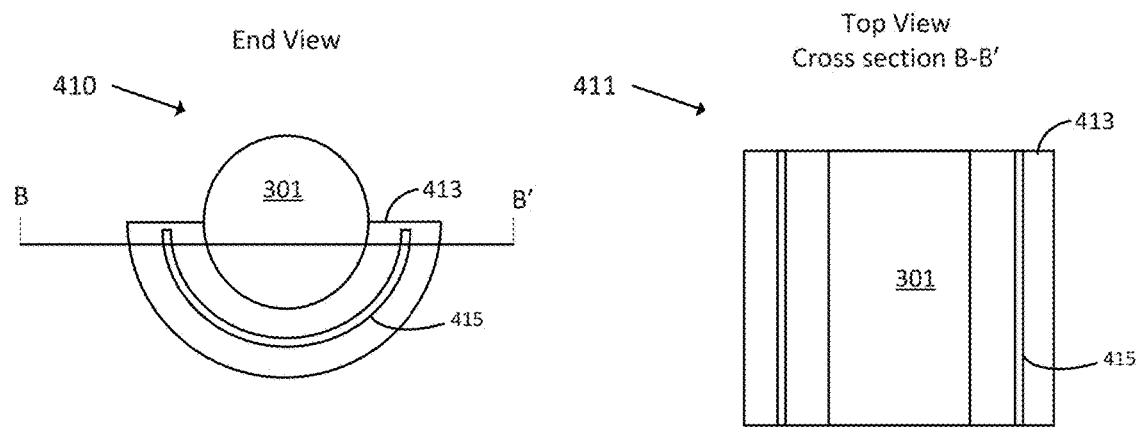
FIGS. 4A-4F are end views and cross-section views of example embodiments of a wrapper on or around a seed.

FIG. 4A is an end view 410 and cross-sectional view 411 of another example wrapper 413, having a shielding layer 415, on or around the seed 301. As shown in cross-sectional view 411, the length of the shielding layer 415 may be coextensive with the length of the wrapper 413 and the length of the seed 301. As shown in cross-sectional view 411, the ends of the shielding layer 415, wrapper 413, and seed 301 may all be flush at one or both ends.

Figure 4B:
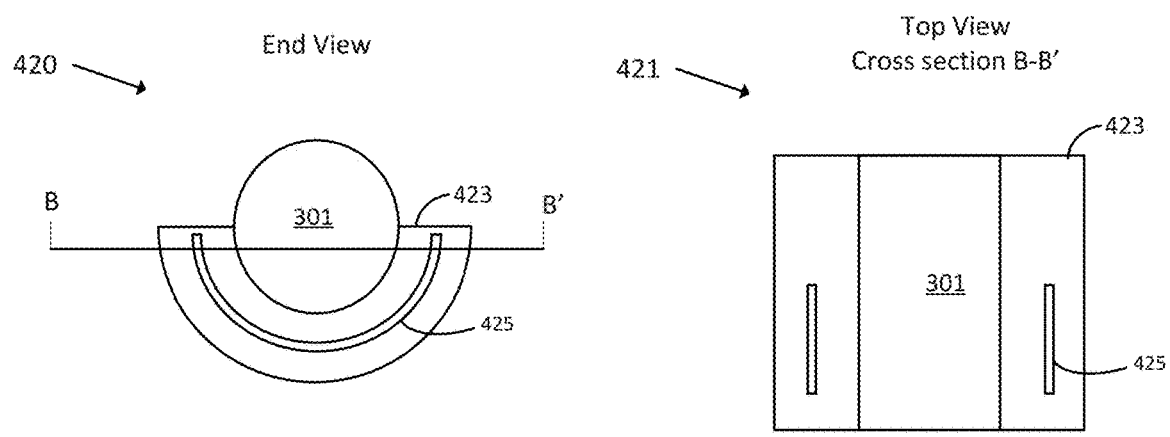

FIG. 4B is an end view 420 and cross-sectional view 421 of another example wrapper 423, having a shielding layer 425, on or around the seed 301. As shown in cross-sectional view 421, in some embodiments, the length of the shielding layer 425 may not be coextensive with the length of the wrapper 423 and/or the length of the seed 301. The ends of the shielding layer 425 may not be flush with the wrapper 423 and/or the seed 301 at one or both ends.

Figure 4C:
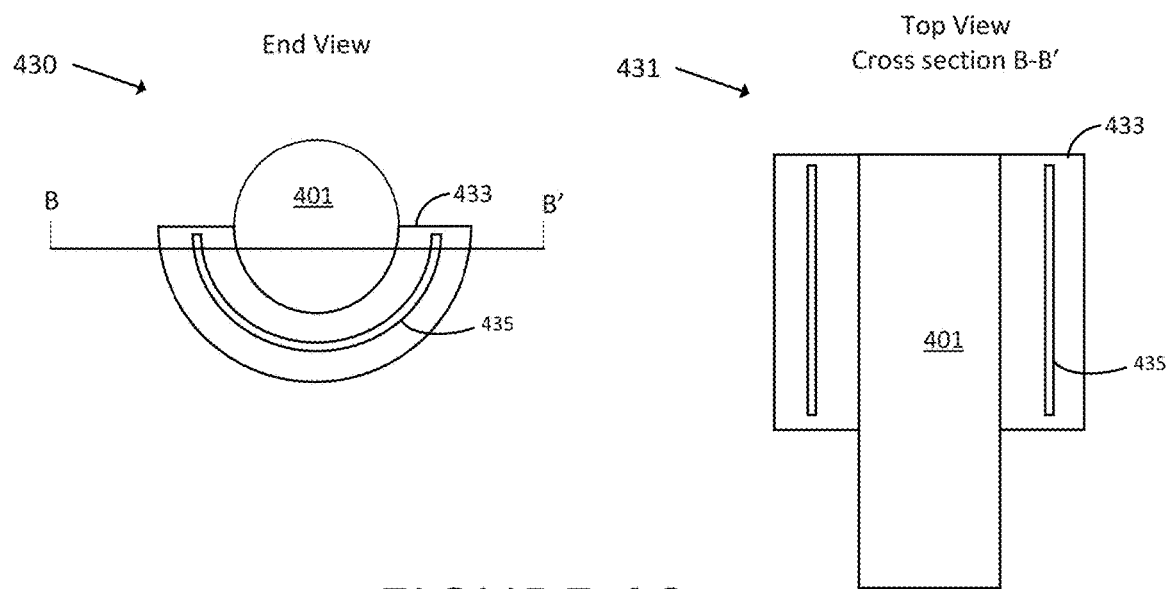

FIG. 4C is an end view 430 and cross-sectional view 431 of another example wrapper 433, having a shielding layer 435, on or around a seed 401. As shown in cross-sectional view 431, in some embodiments, the length of the wrapper 433 may not be coextensive with and/or equal to the length of the seed 401. For example, as shown, the seed 401 may be longer than the wrapper 433 such that one or both ends of the seed 401 extend beyond the end(s) of the wrapper 433. In some embodiments, a seed may be shorter than a wrapper such that neither end or one end of the seed extends beyond the end(s) of the wrapper. Advantageously, wrapping only a portion of the seed 401 with the wrapper 433 may improve the desired dose of radiation delivered to a patient. For example, wrapping only a portion of the seed 401 may directionally shield the radiation emitted from the seed 401 at the wrapped portion while allowing radiation at other unwrapped portions of the seed 401 to be emitted in all directions.

Figure 4D:
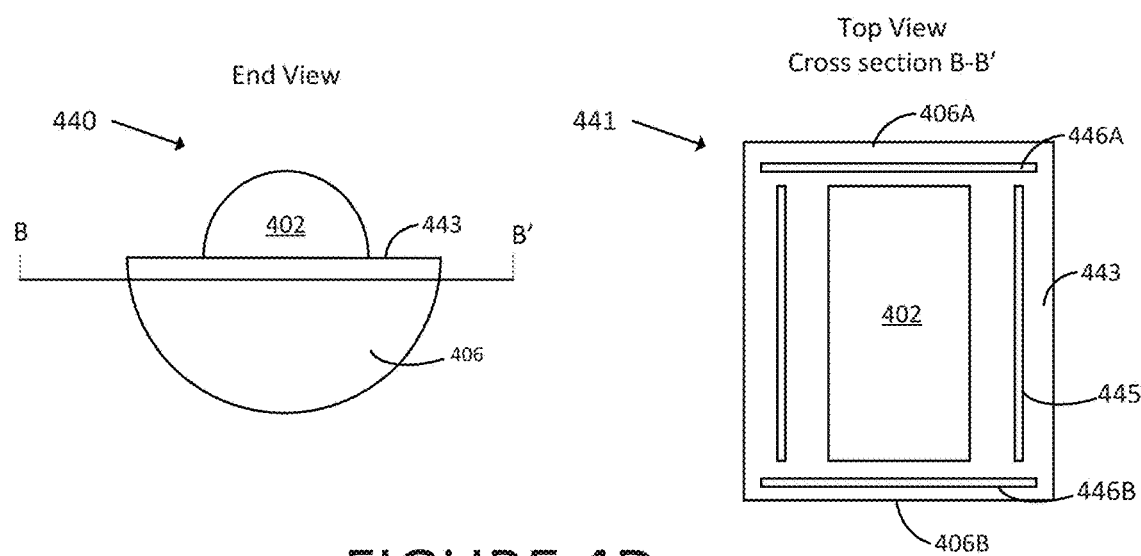

FIG. 4D is an end view 440 and cross-sectional view 441 of another example wrapper 443, having a shielding layer 445, on or around a seed 402. As shown in cross-sectional view 441, in some embodiments, the wrapper 443 includes a cap portion 406 (including cap portion 406A and 406B) at each end. The cap portion(s) 406 may include an additional shielding layer(s) 446 (including shielding layer 446A and shielding layer 446B positioned at opposite ends of the wrapper 443) which may reduce radiation from the seed 402 from extending away from the seed 402 along a direction substantially parallel to a longitudinal axis of the 402 in one or both directions. In some embodiments, the cap portion(s) 406 may facilitate holding the seed 402 in the wrapper 443. For example, the cap portions(s) 406 may be configured to hold the seed 402 in the cavity of the wrapper 443 via a snap fit or friction fit between the cap portion(s) 406.

Figure 4E:
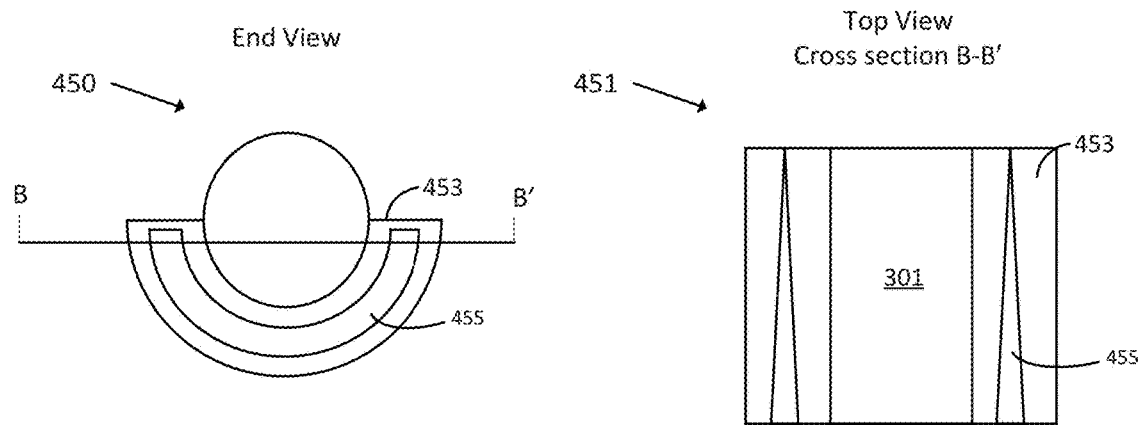

FIG. 4E is an end view 450 and cross-sectional view 451 of another example wrapper 453, having a shielding layer 455, on or around the seed 301. As shown in cross-sectional view 451, in this example embodiment the shielding layer 455 has a variable thickness along a length of the seed 301. For example, the shielding layer 455 is thicker at one end than at the other end such that more radiation from the seed 301 is shielded at one end than at the other end, such as to provide varying radiation prescribed in a radiation treatment plan. Any other variation of thickness of the shielding layer 455 along the length of the seed is contemplated as required or desired, for example according to a dosimetric plan.

Figure 4F:
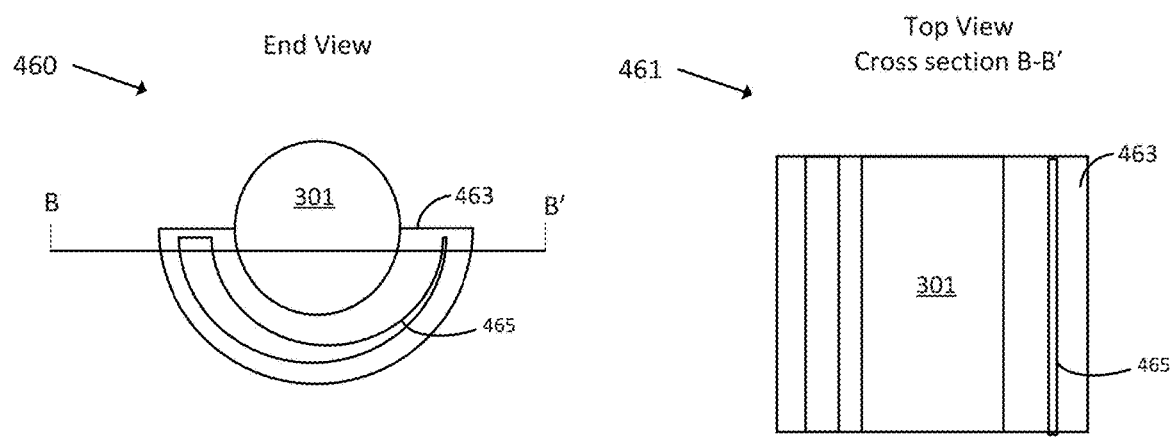

FIG. 4F is an end view 460 and cross-sectional view 461 of another example wrapper 463, having a shielding layer 465, on or around the seed 301. As shown in cross-sectional view 461, in this example embodiment, the shielding layer 465 has a variable thickness around a circumference of the shielded portion of the seed 301. For example, the shielding layer 465 is thicker at one side than at the other side such that more radiation is shielded at one side of the seed 301 than at the other side, such as to provide varying radiation prescribed in a radiation treatment plan. Any variation of thickness of the shielding layer 465 around the circumference of the seed is contemplated as required or desired, for example according to a dosimetric plan.

Figure 5A:
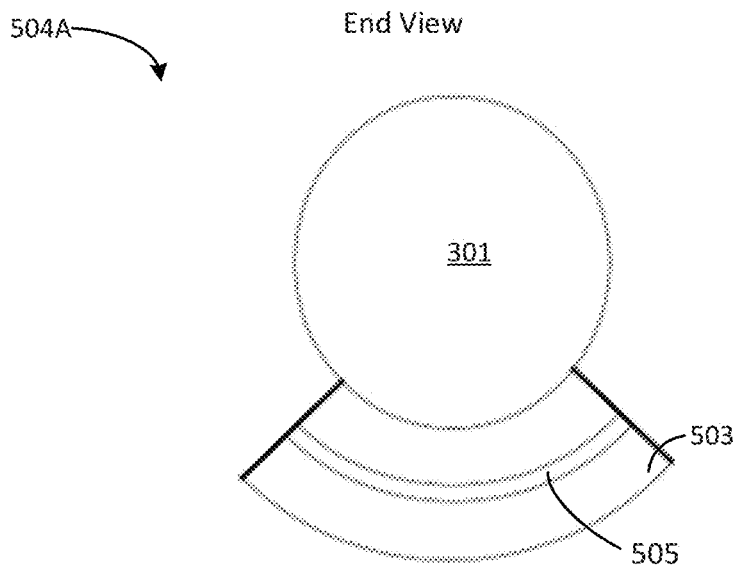
FIGS. 5A-5C are end views of example embodiments of a wrapper on or around a seed.
Figure 5B:
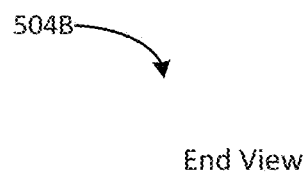
Figure 5B:
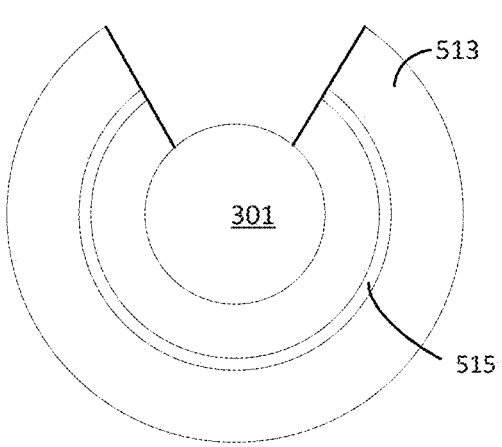
Figure 5C:
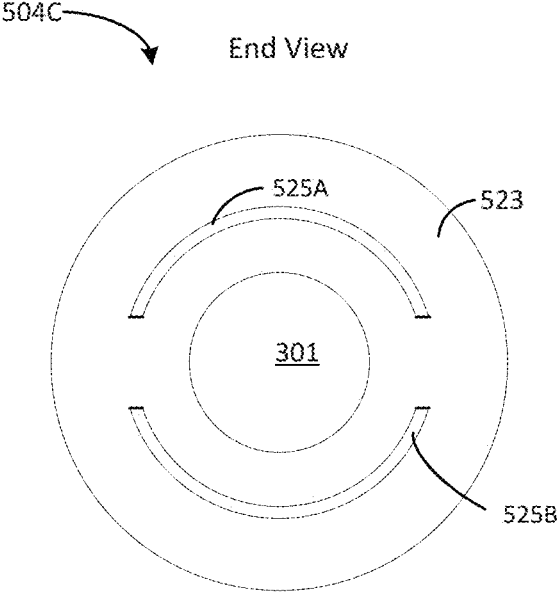

FIGS. 5A-5C are end views of additional examples of wrapped seeds 504 (including wrapped seeds 504A, 504B, 504C), with the wrappers extending around different portions of a circumference of the seed 301. In the example of FIG. 5A, the wrapper 503, including shielding layer 505, extends around less than half (e.g., less than 180 degrees) of a circumference of the seed 301. In the particular example of FIG. 5A, the wrapper 503, and the shielding 505, extend around about 80 degrees of the circumference of the seed 301.

In the example of FIG. 5B, the wrapper 513, including shielding layer 515, extends around more than half of the circumference of the seed 301. In the particular example of FIG. 5B, the wrapper 513, and the shielding 515, extend around about 270 degrees of the circumference of the seed 301.

Wrapping more or less of a circumference of a seed with a wrapper, as shown in FIGS. 5A-5B, may alter the amount and/or direction of radiation emitted from the seed and delivered to a patient, for example, to match a radiation dose prescribed in a radiation treatment plan. Additionally, wrapping more or less of a circumference of a seed with a wrapper may facilitate securing the wrapper to the seed. For example, a wrapper that extends around more than 180 degrees of a seed may secure to the seed via snap fit or friction fit (see FIGS. 3F-3G, for example).

In the example of FIG. 5C, the wrapper 523 includes two shielding layers 525 (including shielding layer 525A and 525B), that are positioned around the seed 301. As shown, the example wrapper 523 extend around an entire circumference of the seed 301, which may advantageously more securely hold the seed 301 in place within the wrapper 523. Furthermore, as shown in FIG. 5C, in some embodiments, the wrapper 523 may include more than one shielding layer 525 such that the shielding layers 525 are physically separate from each other within the wrapper 523 and shield radiation emitted from the seed in different directions and/or by different amounts. Advantageously, the wrapper 523 may thus be configured to deliver specific doses of radiation to a patient in specific directions.

Example Carrier Implementations

Figure 6A:
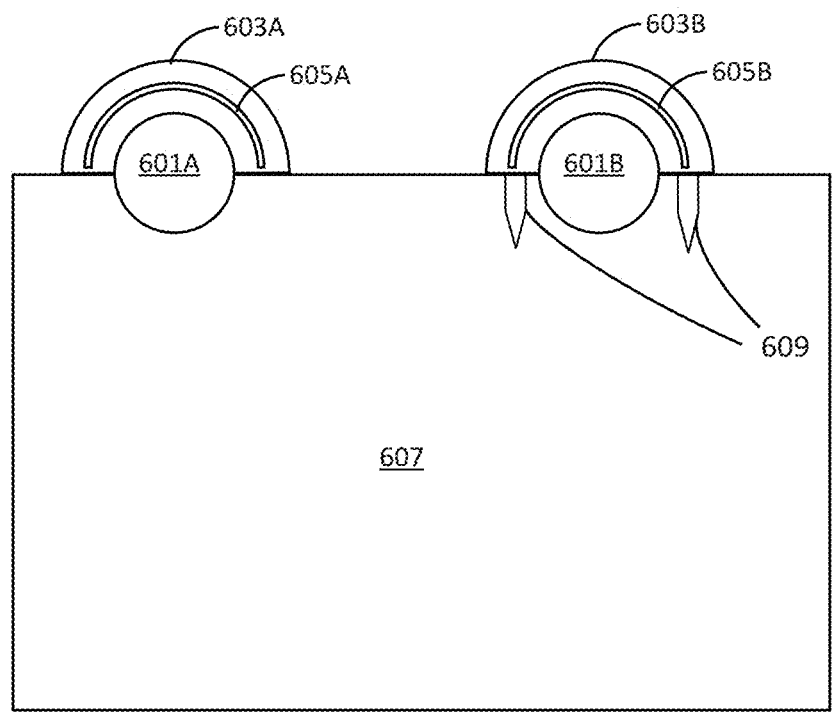
FIGS. 6A-6D illustrate example implementations of wrappers and seeds in a carrier.

FIG. 6A is an end cross-sectional view of a carrier 607 with seeds 601 (including seeds 601A and 601B) embedded therein. As shown, wrappers 603 (including wrappers 603A and 603B) each include a shielding layer 605 (including shielding layers 605A and 605B) configured to shield radiation from about 180 degrees of the seed 601 circumference without shielding radiation directed into the carrier 607. As shown, the seeds 601 are partially embedded within the carrier 607.

In some embodiments, seeds and/or wrappers may be adhered to a carrier using an adhesive property that is inherent to the carrier and/or a separate adhesive. As noted above, certain carrier materials may have an inherent stickiness that adheres the carriers to seeds and/or wrappers. For example, collagen carriers may adhere to seeds and/or wrappers without requiring an additional adhesive material or attachment mechanism.

In the embodiment of FIG. 6A, the wrapper 603B includes fasteners 609. The fasteners 609 may be configured to secure the wrapper 603B (and thus, also the seed 601B) to the carrier 607 by protruding a depth into the carrier 607. The fasteners 609 may be pointed and/or cylindrical in shape such as a nail or rod or may be curved such as a hook. The fasteners 609 may be elongated and may extend along a length of the wrapper 603B. The fasteners 609 may include barbs to prevent retraction of the wrapper 603B from the carrier 607 without compromising easy insertion into the carrier 607.

In some embodiments, in addition to biocompatibility of the carrier, other components of a wrapped seed (e.g., fasteners 609, 619; protrusions 711, connectors 808, 818, 908, 1008, 1028, 1108; protrusions 1011, 1012; anchors 1026; and/or any other components discussed herein) may comprise a biocompatible material. Additionally, in some embodiments these components may be bioresorbable, such as to naturally absorb into tissue at a same or similar rate as the carrier into which the wrapper is attached or embedded. For example, such bioresorbable components (e.g., fasteners with sharp edges) would not be left in the tissue after the carrier is naturally absorbed into the tissue.

In embodiments where a seed is partially embedded within a carrier, a wrapper may be applied to the seed and/or removed from the seed after the seed has already been placed within the carrier. Such an implementation may facilitate the manufacturing of directionally-shielded seed carriers that have already had seeds inserted into the carrier but that lack a directional radiation shield such as a wrapper.

Figure 6B:
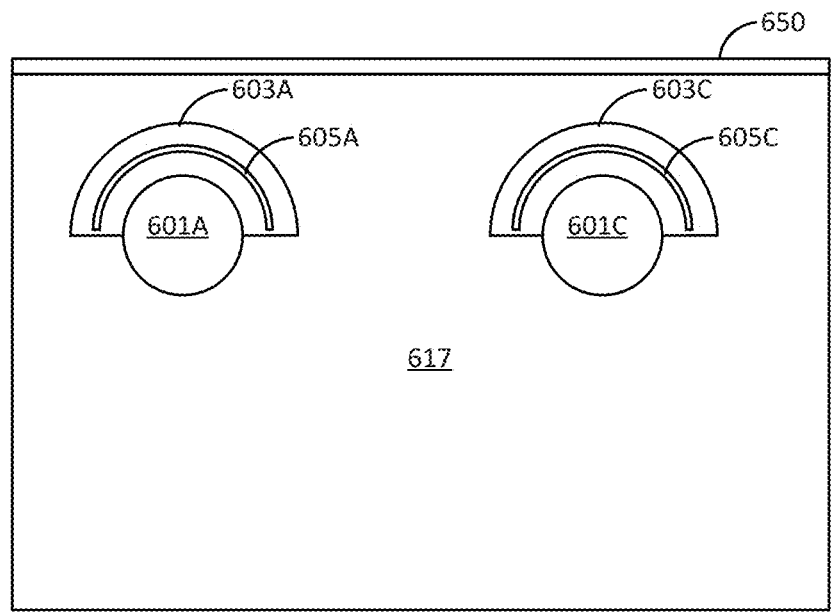

FIG. 6B is an end cross-sectional view of a carrier 617 with seeds 601A and 601C embedded therein. As shown, wrappers 603A and 603C with shielding layers 605A and 605C are positioned around the seeds 601A and 601C to shield radiation emitted from the seeds 601 in certain directions. In this example, the seeds 601 and wrappers 603 are entirely embedded within the carrier 617. In this embodiment, an additional shielding layer 650 is placed on a surface of the carrier 617. The shielding layer 650 may cover an entire surface or only a portion of a surface of the carrier 617. In some embodiments, one or more shielding layers 650 may be placed on more than one surface of the carrier 617. The shielding layer 650 may be implemented in addition to, or in place of, the wrappers 603 and/or the shielding layers 605 of the wrappers 603. The shielding layer 650 may provide additional radioactive shielding to achieve a desired radiation dose (e.g., amount and/or direction of radiation) delivered to a patient. A shielding layer 650 may be implemented in the form of a sticker, for example, that has adhesive properties configured to allow easy application and adherence of the shielding layer 650 to a carrier. In some embodiments, a shielding layer may be configured for customization, such as by cutting or tearing the shielding layer to produce a custom shape and/or size shielding layer that can be placed on or around one or more carriers.

The shielding layer 650 may be secured to the carrier 617 by adhesion. In some embodiments, the shielding layer 650 may be configured with an adhesive property or an adhesive substance to facilitate application and placement to the carrier 607. In some embodiments, the shielding layer 650 may secure to the carrier 617 by an adhesive property of the carrier 617. For example, the carrier 617 may be made of a material, (e.g., collagen) with an inherent stickiness which may bind the shielding layer 650 to the carrier 617. Adhering the shielding layer 650 to the carrier 617 may facilitate quick and simple application of the shielding layer 650 to the carrier 617. For example, a medical professional may place the shielding layer 650 on the carrier 617 during a medical procedure prior to (or after) placing the carrier 617 in a tumor bed of a patient. The medical professional may place the shielding layer 650 on the carrier 617 according to a desired radiation dose or dosimetric plan to be delivered to the patient. For example, the medical professional may place the shielding layer 650 on certain surface of the carrier 617 as desired.

Figure 6C:
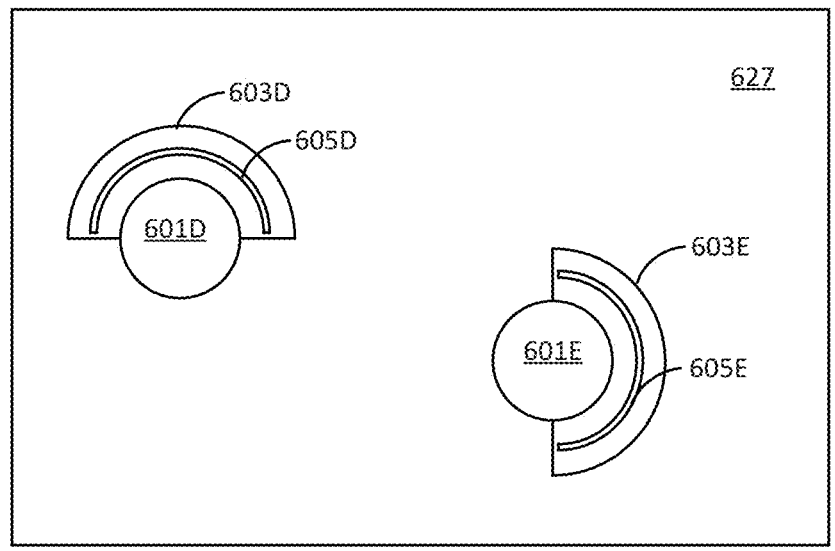

FIG. 6C is an end cross-sectional view of a carrier 627 with seeds 601 (including seeds 601D and 601E) and wrappers 603 (including wrappers 603D and 603E) embedded therein. As shown, the wrapped seeds (e.g., the combination of seeds 601 and corresponding wrappers 603) may be placed at various location throughout the carrier 627. Additionally, the wrapped seeds 603 may be oriented differently from each other to adjust the shielding direction of the respective seeds 601 to non-uniform directions. For example, as shown, the wrapper 603D is positioned so that radiation traveling in an upward direction (relative to the page) is shielded and the wrapper 603E is positioned so that radiation traveling in a rightward direction (relative to the page) is shielded. The wrapped seeds 601 may be placed in this manner to achieve a dosimetric plan.

Figure 6D:
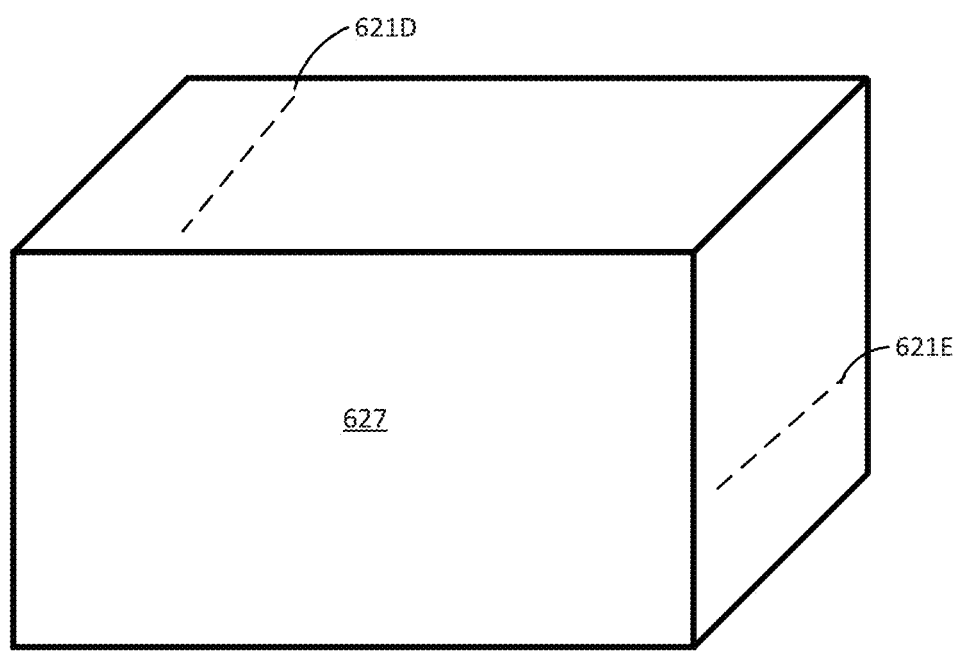

FIG. 6D is a perspective view of carrier 627. In this example, the embedded seeds 601 and wrappers 603 are not visible from an exterior of the carrier 627. A medical professional may desire to know the placement of the seeds 601 or orientation of the wrappers 603 (and any corresponding shielding) within the carrier to know a direction in which the radiation will be shielded and/or be emitted. In this example embodiment, the carrier 627 includes indicators 621D and 621E of direction of shielding of wrapped seeds embedded in the carrier 627. Such indicators may allow a medical professional during a medical procedure to place the carrier (with the wrapped seeds) in the desired position and orientation. For example, indicator 621D indicates that wrapped seed 601D is placed within the carrier 627 beneath the indicator 621D, in alignment with the indicator 621D, and that radiation will be shielded from being emitted from the carrier 627 in a direction of the surface of the carrier 627 on which the indicator 621D is placed (e.g., a generally upward direction relative to the page). As another example, indicator 621E indicates that wrapped seed 601E is placed within the carrier 627 adjacent to the indicator 621E, in alignment with the indicator 621E, and that radiation will be shielded from being emitted from the carrier 627 in a direction of the surface of the carrier 627 on which the indicator 621E is placed (e.g., a generally rightward direction relative to the page).

In some embodiments, indicators may be pad printed or laser printed onto a surface of a carrier. In some embodiments, indicators may be a dotted line as shown in FIG. 6D, for example to match a shape of a cylindrical wrapped seed or may be any other shape or mark to indicate a placement of a wrapped seed within a carrier and/or to indicate a direction of radiation shielding and/or emission. In some embodiments, indicators may include additional information, such as a depth of the wrapped seed, amount of shielding, amount of radiation emitted from the seed, etc.

FIG. 6E is an end cross-sectional view of a carrier 637 with seeds 601F embedded therein. As shown, wrapper 603F (which may be referred to as a carrier wrapper), with shielding layer 605F, is placed on the carrier 637 to shield radiation emitted from the seeds 601F in a generally upward direction (relative to the page). In the embodiment of FIG. 6E, the wrapper 603F includes fasteners 619. The fasteners 619 may be configured to secure the wrapper 603F to the carrier 637 by protruding a depth into the carrier 637. The fasteners 619 may be pointed and/or cylindrical in shape such as a nail or rod or may be curved such as a hook. The fasteners 619 may be elongated and may extend along a length of the wrapper 603F. The fasteners 619 may include barbs to prevent retraction of the wrapper 603F from the carrier 637 without compromising easy insertion into the carrier 637. In some embodiments, the wrapper 603F, may not include fasteners and may secure to the carrier 637 by adhesion. For example, an adhesive property of the wrapper 603F and/or an adhesive property of the carrier 637, which may be made of a collagen with an inherent stickiness, may affix the wrapper 603F to the carrier 637.

In some embodiments, the wrapper 603F may be removably secured to the carrier 637 such that the wrapper 603F may be placed on the carrier 637 and then removed and replaced on the carrier 637. The wrapper 603F may be quickly and easily applied to the carrier 637, for example, by adhesion or by fasteners. For example, a medical professional may place the wrapper 603F on the carrier 637 during a medical procedure prior to placing the carrier 637 in a tumor bed of a patient. The medical professional may place the wrapper 603F on the carrier 637 according to a desired dosimetric plan or radiation dose to be delivered to the patient. In some implementations, a carrier wrapper, such as wrapper 603F, may be used in conjunction with seed wrappers. For example, seeds 601F may each be coupled to wrappers that provide directional shielding, e.g., upward towards the wrapper 603F, to provide even further directional shielding of radiation.

FIG. 6F is a perspective view of a wrapper 603G (which may be referred to as a carrier wrapper), with shielding layer 605G, placed on or around a carrier 647 to shield, in a particular direction, radiation emitted from seed(s) within the carrier 647. In the example embodiment, the wrapper 603G is generally spherical and may be sized to fit on or around the spherical carrier 647.

FIG. 6G is an end cross-sectional view of wrapper 603G. As shown, the wrapper 603G includes fasteners 629 which may be configured to secure the wrapper 603G to the carrier 647, for example, as described with reference to FIG. 6E. In some embodiments, the wrapper 603G may not include fasteners and may secure to the carrier 647 by adhesion. In some embodiments, the wrapper 603G may secure to the carrier 647 by snap fit, or friction fit. For example, a wrapper may have a diameter that is slightly smaller than a diameter of a carrier such that when the carrier is placed within the wrapper, the carrier may deform to a size that is smaller than its natural size and may thus apply an outward force to an inner cavity of the wrapper which force may hold the carrier in place. As another example, a circumference of a wrapper may include more than half (e.g., more than 180 degrees) of the wrapper intact. Thus, a diameter of an opening to an inner cavity of the wrapper may be smaller than the diameter of the inner cavity. Accordingly, a carrier having an outer diameter approximately equal to, or slightly less than, the diameter of the inner cavity of the wrapper may be snapped into the cavity of the wrapper by pressing the seed against the entrance to the cavity of the wrapper to slightly flex the wrapper and/or slightly deform the carrier, so that the carrier enters the cavity of the wrapper. Once in the cavity, the carrier is held in place.

Figure 7A:
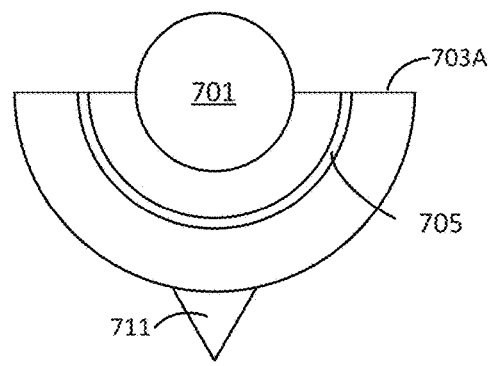
FIGS. 7A-7C illustrate example embodiments of a wrapper with protrusions.
Figure 7B:
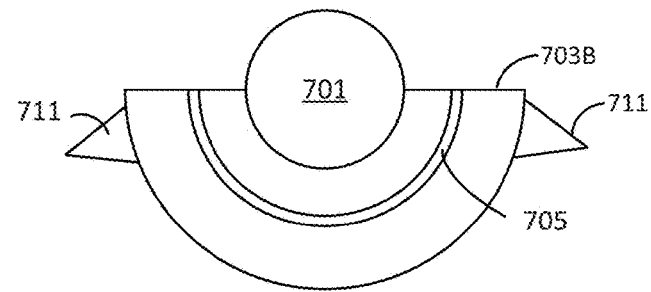
Figure 7C:
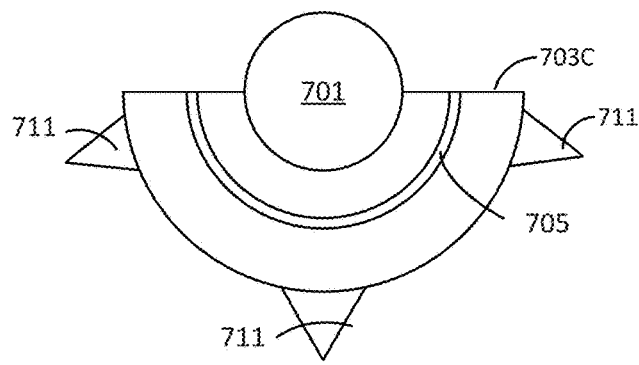

FIGS. 7A-7C illustrate example wrappers 703 (including wrappers 703A, 703B, 703C) with a shielding layer 705 and protrusions 711 positioned at various locations on an outer surface of the wrapper 703. The protrusions 711 may be pointed and/or cylindrical in shape such as a nail or rod or pyramid. The protrusions 711 may be elongated and may extend along a length of the wrapper 703, for example as shown with reference to FIG. 10B.

The protrusions 711 may increase a rotational inertia of the wrapped seeds (e.g., the wrapper 703 and corresponding seed 701) such that a greater force would be required to rotate the wrapped seeds with reference to a carrier in which the wrapped seed is at least partially embedded. For example, when the protrusions 711 are embedded within a carrier, they may prevent the wrapped seed from rotating within the carrier to prevent the direction of radiation shielding from changing after the wrapped seed has been attached to and/or embedded within the carrier.

In some embodiments, the protrusions 711 may indicate a direction of radiation shielding provided by a wrapped seed. For example, as shown and discussed with reference to FIG. 10B, one or more protrusions of a wrapper that is embedded in a carrier may be visible at a side surface of the carrier to indicate, e.g., to a manufacturer and/or doctor, the direction of radiation shielding. For example, as shown in FIG. 7A or 7C, a downward facing protrusion 711 may be flush with a side surface of a carrier or may extend partially out of a carrier such that the downward facing protrusion 711 may be visible from an exterior of the carrier to indicate the orientation of the wrapper 703 within the carrier, although other portions of the wrapper 703 may not be visible within the carrier. Ensuring the direction of radiation shielding, for example, by using protrusions 711 may facilitate quality control when manufacturing the carriers with embedded seeds and wrappers and may also facilitate quality control of healthcare when a healthcare provider is placing the carrier within a patient and may quickly know the direction of radiation shielding.

In some embodiments, the protrusions 711 may be a same material as other portions of the wrapper 703 such as a plastic or polymer, which remains in the tissue after absorption of the carrier in the tissue, such as to reduce seed migration. In some embodiments, the protrusions 711 may extend into the carrier so that the protrusion is adjacent (or closer) to the embedded seed, which may provide even better seed migration control (before and after absorption of the carrier). In other embodiments, such as is discussed above with reference to FIG. 6, the protrusions 711 may comprise a bioresorbable material, such as a material that is configured to be absorbed in tissue at the same or similar rate as the carrier material. In some embodiments, the protrusions 711 may include a high Z material to provide additional radiation shielding.

Example Connector Embodiments

Figure 8A:
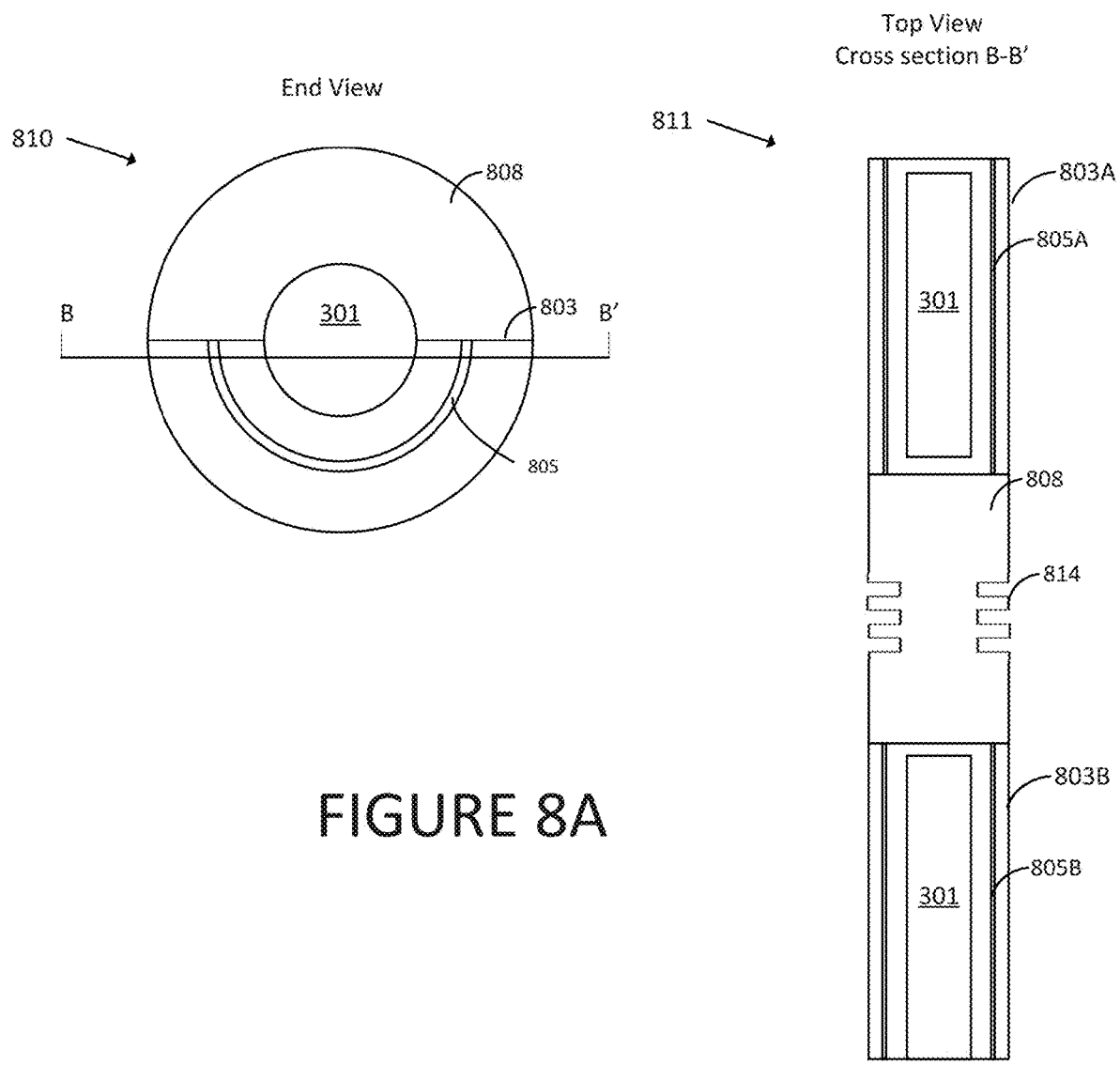
FIGS. 8A-8B are end views and cross-section views of example embodiments of wrappers connected by a connector.

FIG. 8A is an end view 810 and cross-sectional view 811 of multiple example wrappers 803 (including wrappers 803A and 803B), having shielding layers 805 (including shielding layers 805A and 805B), and connected by an example connector 808. As shown in cross-sectional view 811, the wrappers 803A and 803B are connected by a connector 808. In some embodiments, more than two wrappers 803 may be connected by connectors 808 such as three wrappers 803 connected by two connectors 808. The connector 808 may be a same material as the wrappers 803 such as a plastic or polymer. In this example, the connector 808 is a same diameter as the wrappers 803 to which it is connected.

In some embodiments, the connector 808 may be configured to carry a therapeutic agent such as an antimicrobial agent. The connector 808 may carry a therapeutic agent in an interior region of the connector 808 and may include one or holes through which the therapeutic agent may diffuse to reach a tissue site of a patient. The connector 808 may be coated with a therapeutic agent.

In some embodiments, the connector 808 may include a sensor. For example, the connector 808 may include a pH meter configured to detect a pH level at a tissue site of a patient and which may warn of bacterial infection at the tissue site. In some embodiments, the sensor may be powered by biological constituents at a tissue site of a patient such as ions such as sodium, potassium or the like. In some embodiments, the connector 808 may biodegrade over time.

In some embodiments, the connector 808 may include scoring or notches or ribs 814. The ribs 814 may allow the connector 808 to bend while preventing the connector 808 from stretching, compressing or twisting. Advantageously, the ribs 814 may allow the connector 808 to bend, without sacrificing structural durability or integrity, to facilitate placement of a carrier (with the connector 808 and wrappers 803 embedded therein) on uneven surfaces of a tumor bed.

In some embodiments, the connector 808 may comprise a high Z material, for example, shielding layers along an exterior surface of the connector and/or in an interior region of the connector.

Figure 8B:
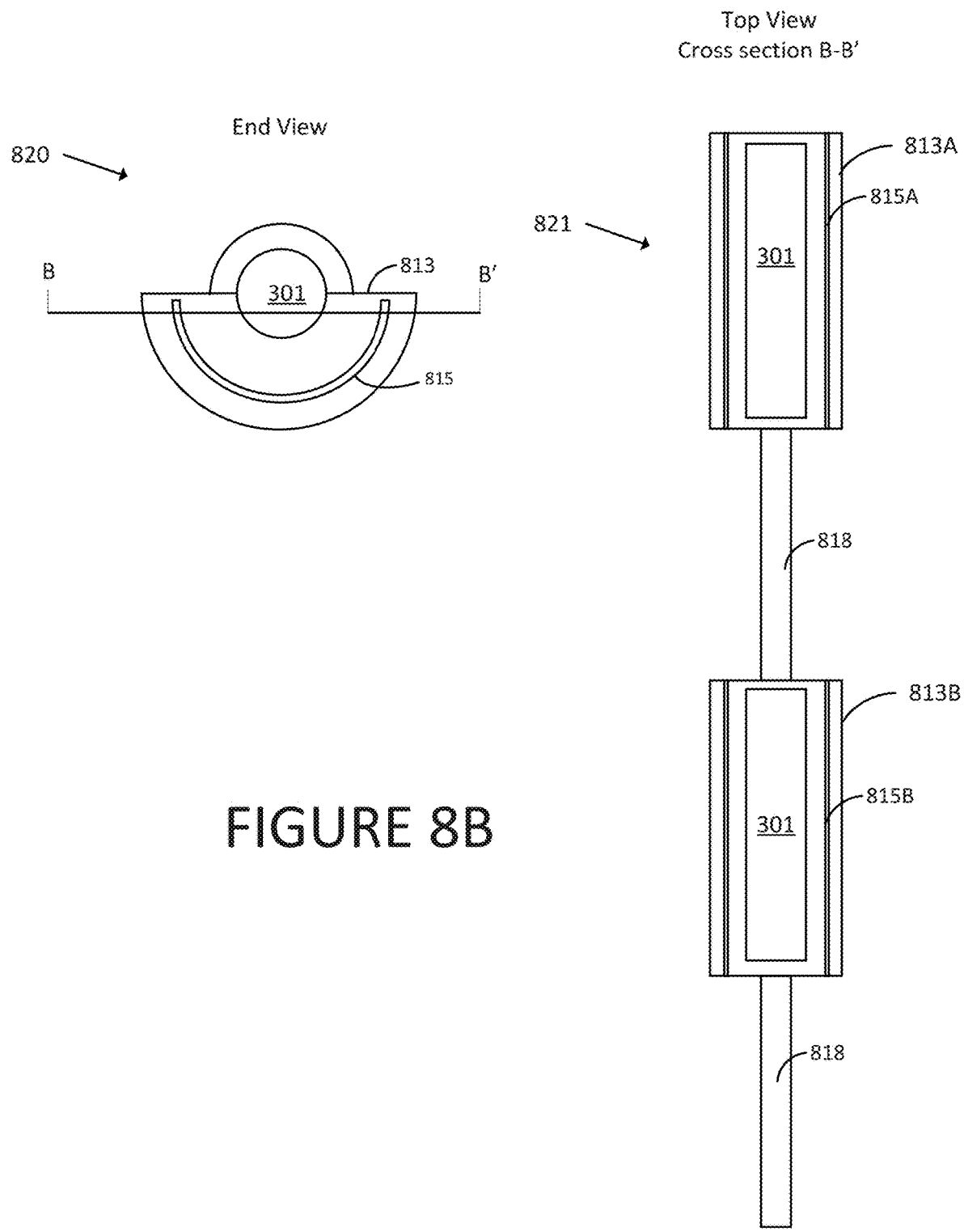

FIG. 8B is an end view 820 and cross-sectional view 821 of multiple example wrappers 813 (including wrappers 813A and 813B), each having shielding layers 815 (including shielding layers 815A and 815B), and connected by example connectors 818. In this example, the connectors 818 have a smaller diameter than the wrappers 813. In some embodiments, the connectors 818 may have a diameter that is large enough to prevent stretching or compressing or twisting when longitudinal or rotational forces are applied to the connector 818, such as when placing the wrappers 813 and corresponding seeds 301 into a carrier, for example as described with reference to FIGS. 10A-10B and 11. In some embodiments, the connectors 818 may have a diameter that is small enough to allow the connector 818 to bend. For example, in implementations where the carrier is placed on a curved surface, the connector 818 may be configured to bend to allow the carrier to conform to the tissue site. In some embodiments, the connectors 818 may be about 0.5 mm in diameter.

In some embodiments, connectors, such as example connectors 808 and 818, may include one or more magnetic resonance imaging (MRI) markers which may be visible in a magnetic resonance image. MRI markers may allow the connector and/or wrapped seed location to be visualized or referenced on a post-operation MR image, such as to confirm dosimetry. This may reduce or eliminate the need to perform additional imaging, such as a post-operation computed tomography (CT) scan, to visualize the seeds and to confirm dosimetry. MRI markers may also facilitate placing the wrapped seeds during MRI-guided brachytherapy. Example MRI markers can include gadolinium, iron oxide, iron platinum, manganese, protein, saline, Conray-60, copper sulfate, liquid vitamin E, fish oil, an agarose gel, or cobalt-chloride.

Figure 9A:
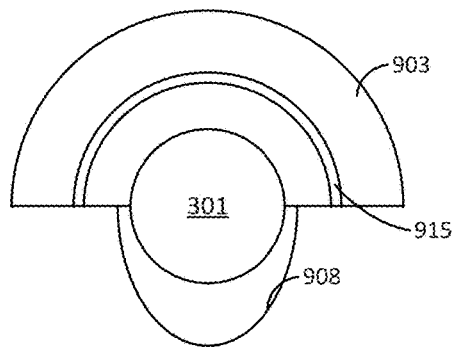
FIGS. 9A-9C are, respectively, an end view, side view, and top view of multiple example wrappers, having shielding layers, and connected by an example connector.
Figure 9B:
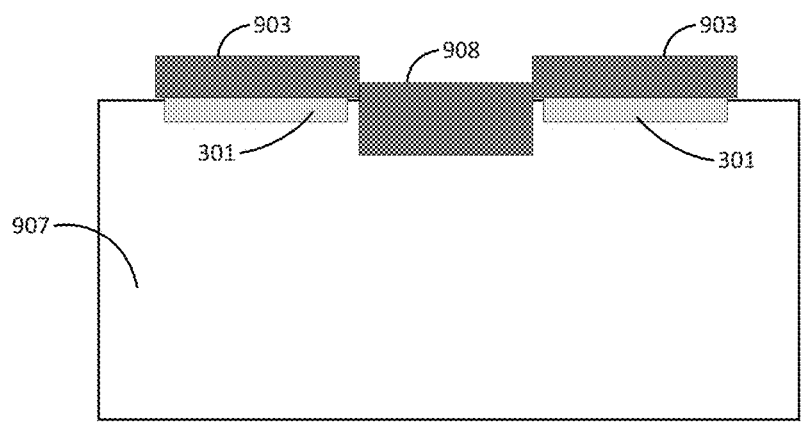
Figure 9C:
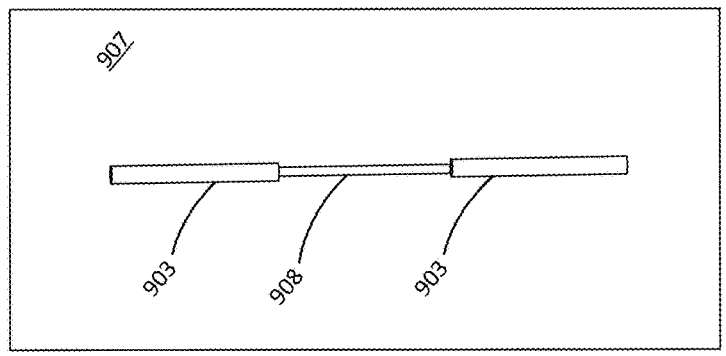

FIGS. 9A-9C are, respectively, an end view, side view, and top view of multiple example wrappers 903, having shielding layers 915, and connected by an example connector 908. As shown, in some embodiments, the connector 908 may not have a circular cross-section. The connector 908, or portion thereof, may extend beyond a seed 301. As shown in FIG. 9B, the connector 908 may extend deeper into a carrier 907 than the seeds 301 and thus facilitate securing the wrappers 903 and seeds 301 to the carrier 907. As shown in FIG. 9C, the wrappers 903 and connector 908 are visible on the top surface of the carrier 907. Thus, in some embodiments, wrappers 903 and/or connectors 908 may be configured to partially extend out of a carrier (e.g., rather than being entirely embedded, such as in some other embodiments discussed herein), to provide a visual cue to the user of the top (e.g., shielded side with wrappers extending) and bottom (unshielded side that is placed on treatment surface of patient). In some embodiments, the wrappers 903 may be secured to top (or other surface) of the carrier 907 using one or more fasteners, such as fasteners 609, 619 discussed with reference to FIG. 6.

Figure 10A:
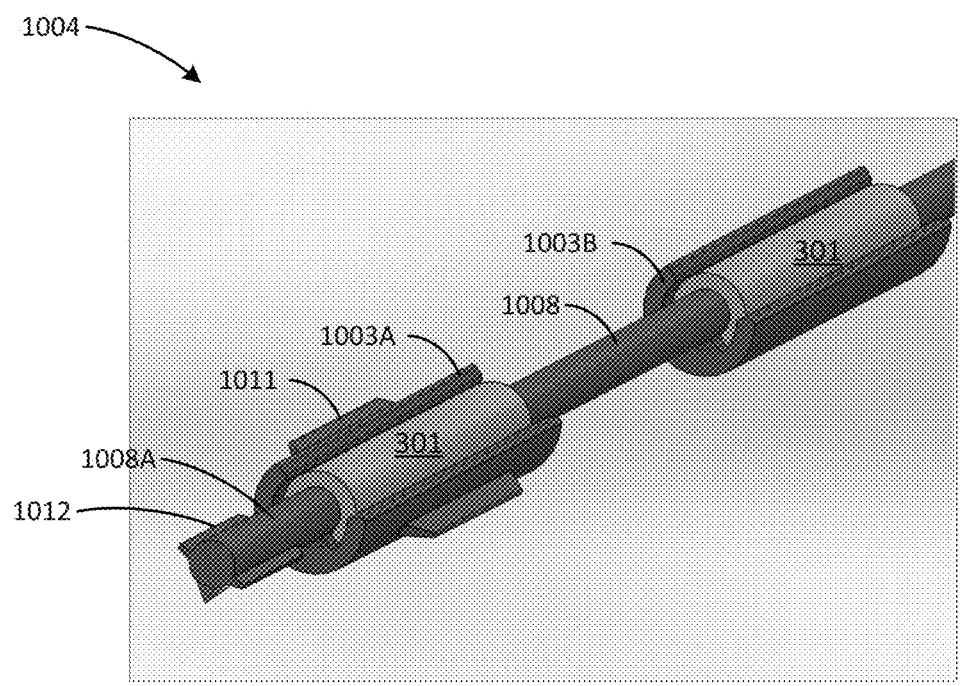
FIG. 10A is a perspective view of a wrappers and seeds connected by connectors.

FIG. 10A is a perspective view of a wrapped seed assembly 1004 comprising multiple wrappers 1003 (including wrapper 1003A and 1003B) connected by multiple connectors 1008 therebetween. As shown, seeds 301 are positioned within respective wrappers 1003. The wrappers 1003 can include shielding layers, for example according to any of the example embodiments discussed herein. In this example, wrapper 1003A includes protrusions 1011 on either side of the wrapper 1003A, which may reduce rotation and/or other movement of the wrapper 1003A after placement within a carrier and maintain a constant orientation of radiation shielding.

The wrappers 1003 are connected by connectors 1008. Additional connectors 1008 extend away from the ends of the wrappers 1003. One or all of the connectors 1008 may include protrusions 1012. For example, as shown, the connector 1008A includes three protrusions 1012 that may further anchor the wrapped seed assembly 1004 by reducing movement of the connector 1008A. In some embodiments, a portion of the wrapped seed assembly 1004, such as a portion of the connector 1008A including the protrusions 1012, may be positioned partially outside of a carrier to provide a visual indication of position and orientation of wrapped seeds within the carrier. This may allow a manufacturer or healthcare provider to know the direction in which radiation will be shielded without viewing the entire wrapped seed assembly 1004.

Figure 10B:
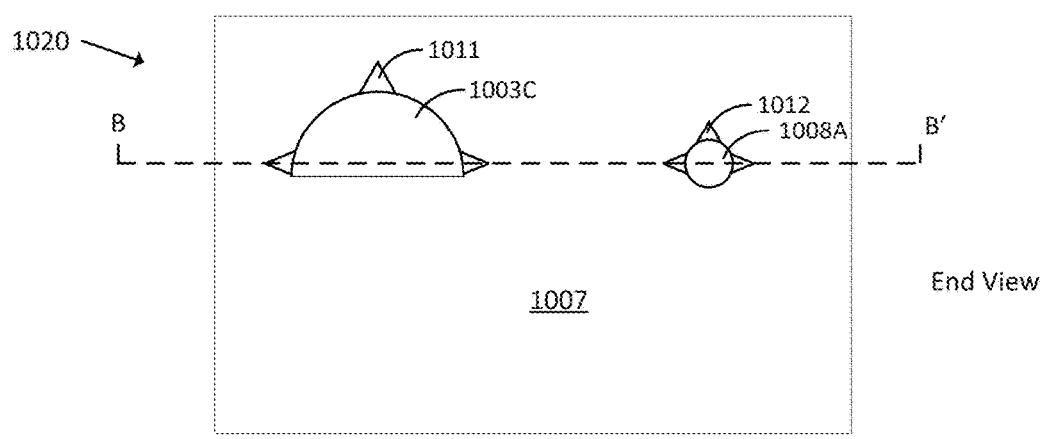
FIG. 10B is an end view and cross-section view of an example implementation of wrappers, seeds and connectors in a carrier.
Figure 10B:
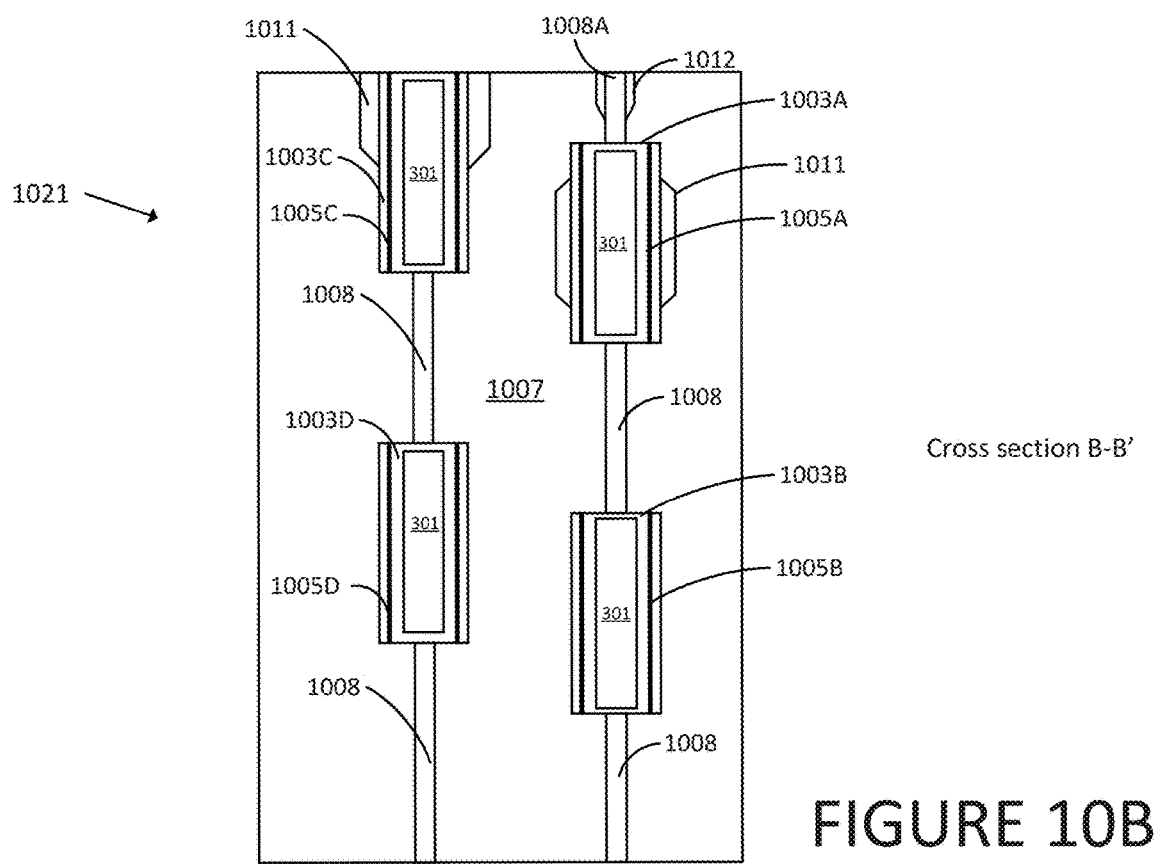

FIG. 10B is an end view 1020 and cross-sectional view 1021 of an example implementation of a carrier 1007 with multiple wrapped seeds embedded therein. In this example, multiple wrappers (including wrappers 1003A, 1003B, 1003C, and 1003D) are loaded with seeds 301 and the wrapped seeds are connected to other wrapped seeds via connectors 1008. The seeds 301, wrappers 1003 and connectors 1008 may be embedded entirely within the carrier 1007 as shown in FIG. 10B, or may be partially embedded in a carrier.

In this example embodiment, the wrappers 1003 include protrusions 1011 and some of the connectors 1008 include protrusions 1012. The protrusions 1011 and 1012 may prevent the wrappers 1003 and/or connectors 1008 from rotating within the carrier 1007. This may prevent a direction of radiation shielding from changing with respect to the carrier 1007 after the wrappers 1003 have been placed within the carrier 1007. As shown, the protrusions 1012 of connector 1008A and the protrusions 1011 of wrapper 1003C are visible from an exterior of the carrier 1007 such as is shown in end view 1020. For example, the protrusions 1011 or protrusions 1012 may be flush with an end (or side) surface of the carrier 1007 to provide a visual indication of a position and/or orientation of a wrapped seed within the carrier. This may allow a manufacturer or healthcare provider to know the direction in which radiation will be shielded without viewing the entire wrapped seed assembly.

Figure 10C:
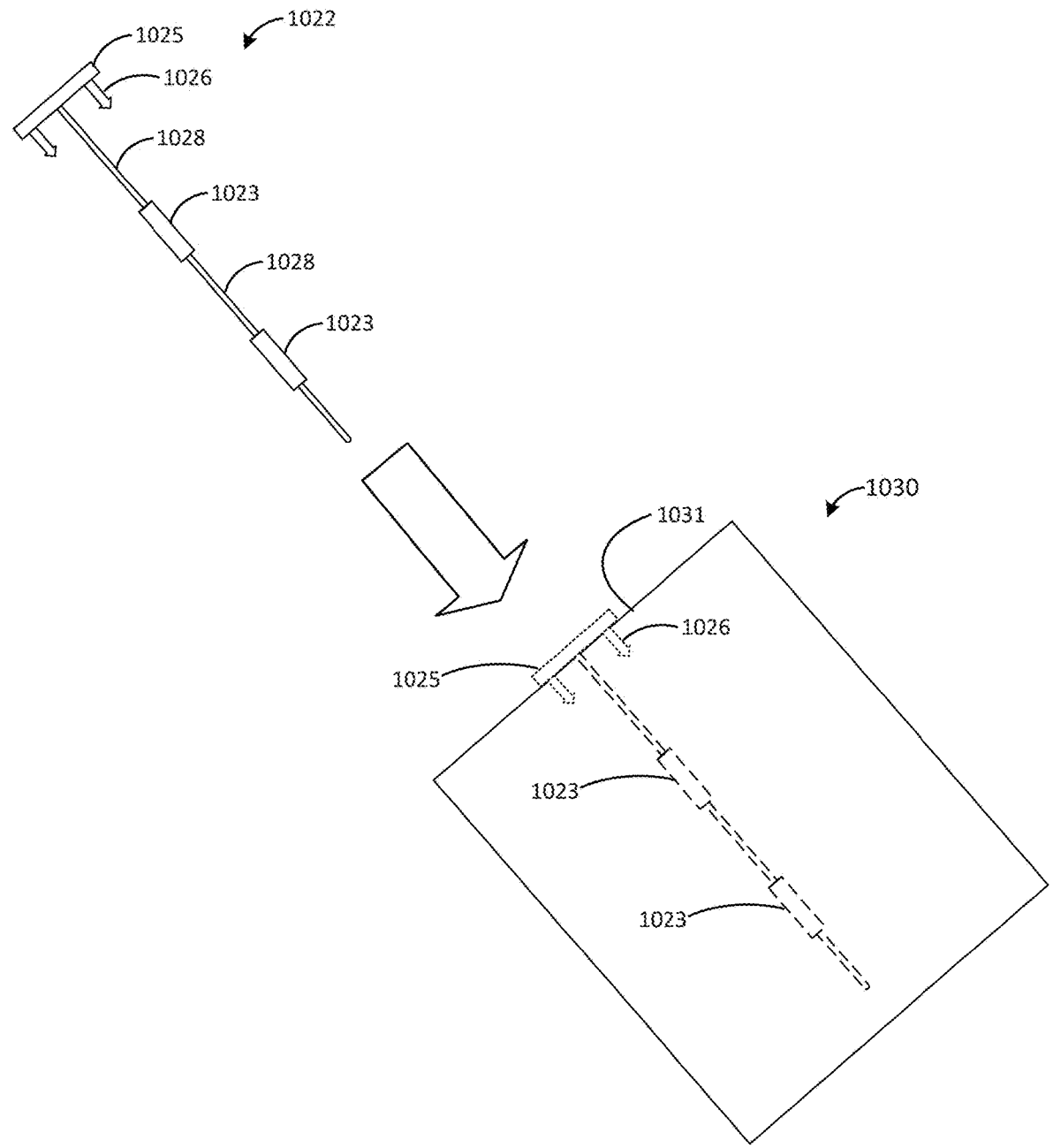
FIG. 10C is a top view of an example wrapped seed assembly positioned for insertion into a side of a carrier.

FIG. 10C is a top view of an example wrapped seed assembly 1022 positioned for insertion into a side of a carrier 1030 (e.g., between a top and bottom surface). In this example, multiple wrappers 1023 are connected by connectors 1028. While not illustrated in FIG. 10C, each of the wrappers 1023 may be loaded with a radioactive seed using any of the processes discussed elsewhere herein. A position retention component of the wrapped seed assembly 1022 comprises a cross member 1025 with anchors 1026 extending towards the carrier 1030. In this embodiment, the wrapped seed assembly 1022 is sized and configured (e.g., lengths of the connectors 1028 are selected) so that when the anchors 1026 are inserted into the side of the carrier 1030 (e.g., the cross member 1025 is abutting a proximal end 1031 of the carrier 1030), the seeds are properly positioned within the carrier 1030. For example, the broken lines in FIG. 10C illustrate portions of the wrapped seed assembly 1022 that are embedded within the carrier 1030. In this example, with the cross member 1025 abutting the proximal end 1031 of the carrier 1030, the radioactive seeds within the wrappers 1023 are properly positioned within the carrier 1030 (e.g., according to a radiation treatment plan). In some embodiments, the cross member 1025 may include visual or tactile features that indicate the orientation of the wrappers and/or seeds, such as to indicate directions where shielding is provided by the wrappers 1023 (which aren't visible once the wrappers 1023 are embedded in the carrier 1030).

In the embodiment of FIG. 10C, the anchors 1026 secure the wrapped seed assembly 1022 within the carrier 1030 by reducing movement of the wrapped seed assembly 1022. In the example of FIG. 10C, the anchors 1026 comprise spikes, but in other embodiments the anchors 1026 may be any other type or configuration of anchoring mechanisms, such as hooks. Additionally, the quantity of anchors 1026 may be varied, such as to include fewer (e.g., one) or additional (e.g., three, four, five, etc.) anchors as part of the wrapped seed assembly 1022.

Figure 11:
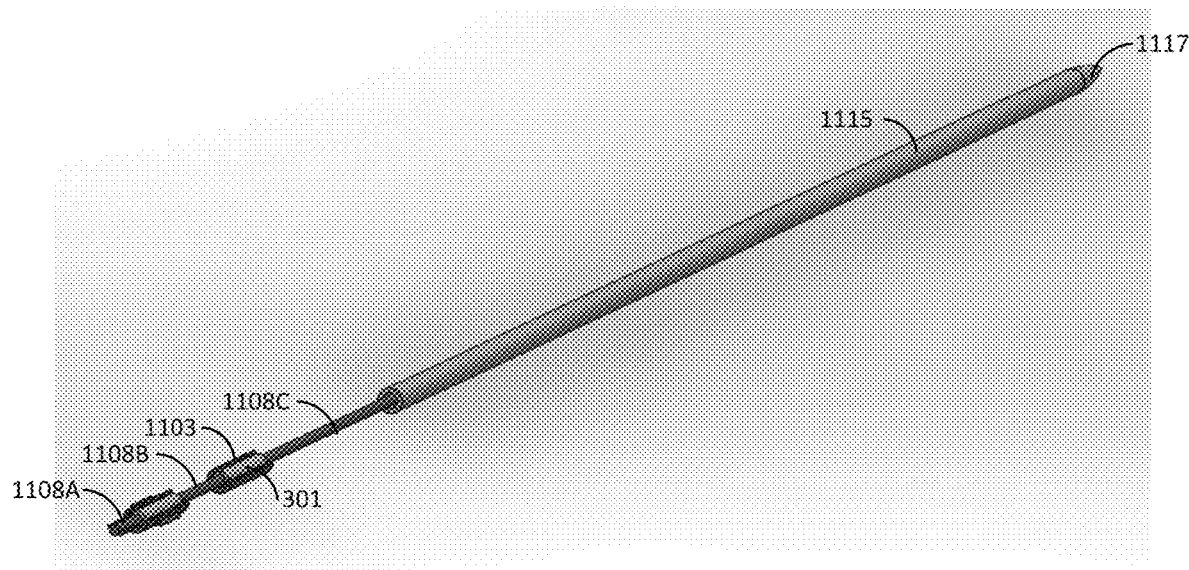
FIG. 11 is perspective view of an example threading apparatus for placing wrappers and seeds in a carrier.

FIG. 11 is a perspective view of an insertion apparatus 1115 used for placing a wrapped seed assembly, comprising multiple wrappers, connectors, and seeds, within a carrier. The insertion apparatus 1115 may be connected to a connector 1108 which in turn may be connected to a wrapper 1103 and/or seed 301. The insertion apparatus 1115 may include a distal tip 1117 which may be pointed or sharp. The insertion apparatus 1115 may be inserted into a carrier via the distal tip 1117. A pointed distal tip 1117 may facilitate insertion into the carrier. The insertion apparatus 1115 may be a length that exceeds a length of a side of a carrier into which a wrapped seed assembly will be placed such that the insertion apparatus may be pushed through the carrier from one side until the distal tip 1117 exits the carrier at the other side. Once the distal tip 1117 has been pushed entirely through the carrier such that the distal tip 1117 exits the other side of the carrier, the distal tip 1117 may be pulled such that the insertion apparatus 1115 is pulled entirely through the carrier. This may cause the adjoining wrapped seed assembly to also be pulled into and at least partially through the carrier. The distal tip 1117 and or insertion apparatus 1115 may be pulled until the wrapped seed assembly is embedded entirely within the carrier or is otherwise positioned relative to the carrier as required or desired. In some embodiments, the distal tip 1117 and or insertion apparatus 1115 may be pulled until an end of a connector 1108A is flush with a side of the carrier such as shown in FIG. 10B. Once the wrapped seed assembly is positioned relative to the carrier as required or desired, a portion of one or more of the connectors 1108 may be partially embedded within the carrier and may be partially protruding from the carrier. For example, connector 1108A and/or connector 1108B may be partially protruding from the carrier after the wrapped seed assembly has been positioned relative to the carrier as required or desired. The portions of any connectors 1108 that are protruding from the carrier after insertion may be cut such that an end of the connector(s) 1108 are flush with an end of the carrier and such that no portion of the connector(s) 1108 extend beyond a side surface of the carrier. In some embodiments, portions of wrappers that are protruding from the carrier after positioning may also be cut as described above with reference to connectors.

Additional Embodiments

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, the use of particular terminology when describing certain features or aspects of the invention should not be taken to imply that the terminology is being redefined herein to be restricted to including any specific characteristics of the features or aspects of the invention with which that terminology is associated. The scope of the invention should therefore be construed in accordance with the appended claims and any equivalents thereof.

What is claimed is:

1. A carrier system for delivering directional radiation treatment to a tissue site according to a dosimetric plan, the carrier system comprising:
a biocompatible carrier comprising collagen configured to be placed on an exposed treatment surface of a surgically-created cavity in mammalian tissue; and
a wrapped seed assembly including:
a plurality of wrapped seeds each comprising:
a cylindrical radioactive seed; and
a substantially cylindrically shaped apparatus having a length at least as long as the radioactive seed and having a central longitudinal cavity wherein the cylindrical radioactive seed is positioned, wherein the substantially cylindrically shaped apparatus includes a shielding layer extending along the length of the substantially cylindrically shaped apparatus, the shielding layer comprising a high-z material; and
one or more connectors configured to secure and position respective pairs of wrapped seeds in a predetermined spaced-apart arrangement according to the dosimetric plan;
wherein the wrapped seed assembly, including the plurality of wrapped seeds spaced apart by the one or more connectors, is positioned within the biocompatible carrier according to the dosimetric plan.

2. The carrier system of claim 1, wherein a respective substantially cylindrically shaped apparatus is configured to attach to a respective radioactive seed via snap fit or friction fit to cover at least a portion of an exterior surface of the respective radioactive seed.

3. The carrier system of claim 1, wherein at least one of the wrapped seeds comprises one or more protrusions configured to secure the wrapped seed assembly to the biocompatible carrier.

4. The carrier system of claim 1, wherein at least one of the wrapped seeds comprises one or more protrusions configured to increase a rotational inertia to reduce rotation of the wrapped seed assembly relative to the biocompatible carrier.

5. The carrier system of claim 1, wherein the shielding layer comprises a plurality of individual, discrete layers of one or more high Z materials.

6. The carrier system of claim 1, wherein the shielding layer is embedded in an interior region of the substantially cylindrically shaped apparatus.

7. The carrier system of claim 1, wherein the shielding layer is positioned on an exterior surface of the substantially cylindrically shaped apparatus.

8. The carrier system of claim 1, wherein the shielding layer has a half value layer (HVL) of two.

9. The carrier system of claim 1, wherein the substantially cylindrically shaped apparatus has a thickness of between 0.18 mm and 0.22 mm, and the shielding layer has a thickness of between 0.026 mm and 0.036 mm.

10. The carrier system of claim 1, wherein the shielding layer has a thickness of between 0.01 mm and 0.06 mm.

11. The carrier system of claim 1, wherein the substantially cylindrically shaped apparatus comprises plastic or polymer.

12. The carrier system of claim 1, wherein the one or more connectors are cylindrically shaped and have a diameter of 0.5 mm.

13. The carrier system of claim 1, wherein the one or more connectors comprise therapeutic agents.

14. The carrier system of claim 1, wherein at least one of the one or more connectors comprise one or more protrusions visible from an exterior of the biocompatible carrier to indicate a direction in which radiation emitted from the radioactive seed is shielded by the shielding layer.

15. A method for preparing a carrier to deliver directional radiation treatment to a tissue site according to a dosimetric plan, the method comprising:
positioning a wrapped seed assembly within a biocompatible carrier comprising collagen according to a dosimetric plan;
wherein the wrapped seed assembly includes:
a plurality of wrapped seeds each comprising:
a cylindrical radioactive seed; and
a substantially cylindrically shaped apparatus having a length at least as long as the radioactive seed and having a central longitudinal cavity wherein the cylindrical radioactive seed is positioned, wherein the substantially cylindrically shaped apparatus includes a shielding layer extending along the length of the substantially cylindrically shaped apparatus, the shielding layer comprising a high-z material; and
one or more connectors configured to secure and space respective pairs of wrapped seeds according to the dosimetric plan.

16. The method of claim 15, further comprising attaching a respective substantially cylindrically shaped apparatus to a respective radioactive seed via snap fit or friction fit to cover at least a portion of an exterior surface of the respective radioactive seed.

17. The method of claim 15, wherein at least one of the wrapped seeds comprises one or more protrusions configured to secure the wrapped seed assembly to the biocompatible carrier.

18. The method of claim 15, wherein at least one of the wrapped seeds comprise one or more protrusions configured to increase a rotational inertia to reduce rotation of the wrapped seed assembly relative to the biocompatible carrier.

19. The method of claim 15, wherein the shielding layer comprises a plurality of individual, discrete layers of one or more high Z materials.

* * * * *